United States Patent
Majumdar et al.

(10) Patent No.: US 8,415,153 B2
(45) Date of Patent: Apr. 9, 2013

(54) DIFFERENTIATION AND ENRICHMENT OF ISLET-LIKE CELLS FROM HUMAN PLURIPOTENT STEM CELLS

(75) Inventors: Anish Sen Majumdar, Mumbai (IN); JianJie Jiang, Sunnyvale, CA (US); Melinda Au, Fremont, CA (US)

(73) Assignee: Geron Corporation, Menlo Park, CA (US)

( * ) Notice: Subject to any disclaimer, the term of this patent is extended or adjusted under 35 U.S.C. 154(b) by 0 days.

(21) Appl. No.: 12/303,895

(22) PCT Filed: May 25, 2007

(86) PCT No.: PCT/US2007/012489
§ 371 (c)(1),
(2), (4) Date: Feb. 12, 2009

(87) PCT Pub. No.: WO2007/149182
PCT Pub. Date: Dec. 27, 2007

(65) Prior Publication Data
US 2010/0240130 A1    Sep. 23, 2010

Related U.S. Application Data

(60) Provisional application No. 60/815,111, filed on Jun. 19, 2006.

(51) Int. Cl.
*C12N 5/00* (2006.01)
*C12N 5/071* (2010.01)
*C12N 5/02* (2006.01)

(52) U.S. Cl. ............................. 435/377; 435/366; 435/325

(58) Field of Classification Search .................. 435/325, 435/366, 377
See application file for complete search history.

(56) References Cited

U.S. PATENT DOCUMENTS

| | | | |
|---|---|---|---|
| 4,378,016 A | 3/1983 | Loeb | |
| 4,391,909 A | 7/1983 | Lim | |
| 4,439,521 A | 3/1984 | Archer et al. | |
| 4,797,213 A | 1/1989 | Parisius et al. | |
| 5,674,289 A | 10/1997 | Fournier et al. | |
| 5,834,308 A | 11/1998 | Peck et al. | |
| 5,888,705 A | 3/1999 | Rubin et al. | |
| 5,888,816 A | 3/1999 | Coon et al. | |
| 5,902,577 A | 5/1999 | Asfari et al. | |
| 5,919,703 A | 7/1999 | Mullen et al. | |
| 5,928,942 A | 7/1999 | Brothers | |
| 5,935,852 A | 8/1999 | Follettie et al. | |
| 6,023,009 A | 2/2000 | Stegemann et al. | |
| 6,090,622 A | 7/2000 | Gearhart et al. | |
| 6,197,945 B1 | 3/2001 | Edlund | |
| 6,200,806 B1 | 3/2001 | Thomson | |
| 6,326,201 B1 | 12/2001 | Fung et al. | |
| 6,436,704 B1 | 8/2002 | Roberts et al. | |
| 6,610,535 B1 | 8/2003 | Lu et al. | |
| 6,946,293 B1 | 9/2005 | Lu et al. | |
| 7,033,831 B2 | 4/2006 | Fisk et al. | |
| 7,326,572 B2 | 2/2008 | Fisk et al. | |
| 7,510,876 B2 | 3/2009 | D'Amour et al. | |
| 2003/0032183 A1 | 2/2003 | Sheridan | |
| 2004/0191901 A1 | 9/2004 | Assady et al. | |
| 2004/0259244 A1 | 12/2004 | Scharp et al. | |
| 2005/0054102 A1 | 3/2005 | Wobus et al. | |
| 2005/0158853 A1 | 7/2005 | D'Amour et al. | |
| 2005/0266554 A1 | 12/2005 | D'Amour et al. | |
| 2006/0003313 A1 | 1/2006 | D'Amour et al. | |
| 2006/0275900 A1 | 12/2006 | Presnell et al. | |
| 2006/0276420 A1 | 12/2006 | Keller et al. | |
| 2008/0145889 A1 | 6/2008 | Fisk et al. | |
| 2009/0093055 A1 | 4/2009 | Fisk et al. | |

FOREIGN PATENT DOCUMENTS

| | | |
|---|---|---|
| CA | 2466342 | 5/2003 |
| WO | WO 98/14592 A2 | 4/1998 |
| WO | WO 99/20741 A1 | 4/1999 |
| WO | WO 00/47720 A2 | 8/2000 |
| WO | WO 00/47721 A2 | 8/2000 |
| WO | WO 00/72885 A2 | 12/2000 |
| WO | WO 00/78929 A1 | 12/2000 |
| WO | WO 01/11011 A2 | 2/2001 |
| WO | WO 01/39784 A1 | 6/2001 |
| WO | WO 01/51610 A1 | 7/2001 |
| WO | WO 01/51616 A2 | 7/2001 |
| WO | WO 01/77300 A2 | 10/2001 |
| WO | WO 01/81549 A2 | 11/2001 |
| WO | WO 02/059278 A2 | 8/2002 |
| WO | WO 02/074946 A2 | 9/2002 |
| WO | WO 02/074948 A2 | 9/2002 |
| WO | WO 02/079457 A1 | 10/2002 |
| WO | WO 02/086107 A2 | 10/2002 |
| WO | WO 02/092756 A2 | 11/2002 |
| WO | WO 02/096203 A1 | 12/2002 |
| WO | WO 03/029445 A1 | 4/2003 |
| WO | WO-2007/149182 | 12/2007 |

OTHER PUBLICATIONS

Docherty et al., Semin. Cell Dev. Biol. 18(6): 827-838, 2007.*
Valdimarsdottir et al., APMIS, vol. 113(11-12), pp. 773-789, 2005.*
Inami et al., 2010, Immunology and Cell Biology, pp. 1-8.*
McLean et al., 2007, Stem Cells, vol. 25, pp. 29-38.*
Xu et al., 2011, Mech. of Develop., ePUB, pp. 1-16.*
Ruchelli ED, Color Atlas of Fetal and Neonatal Histology, Springer Publishing, Cover page and p. 78.*

(Continued)

*Primary Examiner* — Peter Paras, Jr.
*Assistant Examiner* — David A Montanari
(74) *Attorney, Agent, or Firm* — Leslie A. Mooi

(57) ABSTRACT

Methods for differentiating human pluripotent stem cells into islet-like cells are provided. In certain embodiments, the methods utilize sequential culturing of the human pluripotent stem cells with certain factors to produce islet-like cells. In certain embodiments, the population of cells produced by the methods is further enriched for islet-like cells.

24 Claims, 8 Drawing Sheets

OTHER PUBLICATIONS

Abraham, E. et al., "Insulinotropic Hormone Glucagon-Like Peptide-1 Differentiation of Human Pancreatic Islet-Derived Progenitor Cells into Insulin-Producing Cells," *Endocrinol.* 143(8):3152-61 (Aug. 2002).

Amit, M. & Itskovitz-Eldor, J., "Derivation and Spontaneous Differentiation of Human Embryonic Stem Cells," *J. Anat.* 200:225-32 (2002).

Apelqvist, A. et al., "Notch Signalling Controls Pancreatic Cell Differentiation," *Nature* 400(6747):877-81 (Aug. 1999).

Assady, S. et al., "Insulin Production by Human Embryonic Stem Cells," *Diabetes* 50(8):1691-7 (Aug. 2001).

Beattie, G. et al., "Regulation of Proliferation and Differentiation of Human Fetal Pancreatic Islet Cells by Extracellular Matrix, Hepatocyte Growth Factor, and Cell-Cell Contact," *Diabetes* 45:1223-8 (Sep. 1996).

Berná, G. et al., "Stem cells and diabetes," *Biomed. Pharmacother.* 55(4):206-12 (2001).

Blyszczuk, P. et al., "Expression of Pax4 in Embryonic Stem Cells Promotes Differentiation of Nestin-Positive Progenitor and Insulin-Producing Cells," *Proc. Natl. Acad. Sci. USA* 100(3):998-1003 (2003).

Bonner-Weir, S. et al., "In vitro cultivation of human islets from expanded ductal tissue," *Proc. Natl. Acad. Sci.* 97:7999-8004 (2000).

Bretzel, R. et al., "Islet Transplantation: Present Clinical Situation and Future Aspects," *Exp Clin Endocrinol Diabetes* 109(Suppl 2):S384-99 (2001).

Caricasole, A. et al., "Bone morphogenetic proteins (BMPs) induce epithelial differentiation of NT2D1 human embryonal carcinoma cells," *Int. J. Dev. Biol.* 44:443-50 (2000).

D'Amour, K. et al., "Efficient differentiation of human embryonic stem cells to definitive endoderm," *Nat. Biotech.* 23(12):1534-41 (2005).

D'Amour, K. et al., "Production of pancreatic hormone-exresssing endocrine cells from human embryonic stem cells," *Nat. Biotech.* 24(11):1392-401 (2006).

Demeterco, C. et al., "A role for activin A and betacellulin in human fetal pancreatic cell differentiation and growth," *J. Clin. Endocrin. Metabol.* 85:3892-7 (2000).

Deutsch, G. et al., "A Bipotential Precursor Population for Pancreas and Liver Within the Embryonic Endoderm," *Development* 128(6):871-81 (2001).

Gradwohl, G. et al.,"Neurogenin3 is Required for the Development of the Four Endocrine Cell Lineages of the Pancreas," *Proc. Natl. Acad. Sci. USA* 97(4):1607-11 (Feb. 2000).

Habener, J. et al., "Minireview: transcriptional regulation in pancreatic development," *Endocrinol.* 146:1025-34 (2005).

Hayek, A. & Beattie, G., "Experimental Transplantation of Human Fetal and Adult Pancreatic Islets," *J. Clin. Endocrinol. Metab.* 82(8):2471-5 (1997).

Hori,Y. et al., "Growth Inhibitors Promote Differentiation of Insulin-Producing Tissue from Embryonic Stem Cells," *Proc. Natl. Acad. Sci. USA* 99(25):16105-10 (Dec. 2002).

Jacobson, L. et al., "Differentiation of Endoderm Derivatives, Pancreas and Intestine, from Rhesus Embryonic Stem Cells," *Transplant. Proc.* 33(1-2):674 (2001).

Johansson, B. & Wiles, M., "Evidence for involvement of activin A and bone morphogenetic protein 4 in mammalian mesoderm and hematopoietic development," *Mol. Cel. Biol.* 15:1141-51 (1995).

Jung, J. et al., "Initiation of mammalian liver development from endoderm by fibroblast growth factors," *Science* 284:1998-2003 (Jun. 18, 1999).

Kaczorowski, D. et al., "Glucose-Resposive Insulin-Producing Cells from Stem Cells," *Diabetes Metab. Res. Rev.* 18(6):442-50 (Nov./Dec. 2002).

Kania, G. et al., "The generation of insulin-producing cells from embryonic stem cells—a discussion of controversial findings," *Int. J. Dev. Biol.* 48:1061-4 (2004).

Keymeulen, B. et al., "Implantation of Standardized Beta-Cell Grafts in a Liver Segment of IDDM Patients: Graft and Recipient Characteristics in Two Cases of Insulin-Independence Under Maintenance Immunosuppression for Prior Kidney Graft," *Diabetologia* 41:452-9 (1998).

Kim, S. & Hebrok, M., "Intercellular Signals Regulating Pancreas Development and Function," *Genes Dev.* 15:111-27 (2001).

Ku, H. et al., "Committing embryonic stem cells to early endocrine pancreas in vitro," *Stem Cells* 22:1205-17 (2004).

Kubo, A. et al., "Development of definitive endoderm from embryonic stem cells in culture," *Development* 131:1651-62 (2004).

Lim, J. & Bodnar, A., "Proteome analysis of conditioned medium from mouse embryonic fibroblast feeder layers which support the growth of human embryonic stem cells," *Proteomics* 2:1187-203 (2002).

Lumelsky, N. et al., "Differentiation of Embryonic Stem Cells to Insulin-Secreting Structures Similar to Pancreatic Islets," *Science* 292:1389-94 (May 2001).

Mashima, H. et al., "Betacellulin and activin A coordinately convert amylase-secreting pancreatic AR42J cells into insulin-secreting cells," *J. Clin. Invest.* 97:1647-54 (1996).

Oberholzer, J. et al., "Clinical Islet Transplantation: A Review," *Ann. NY Acad. Sci.* 875:189-99 (1999).

Odorico, J. et al., "Pancreatic Gene Expression in Differentiating Embryonic Stem Cells," Keystone Symposium on Stem Cells, Keystone, Colorado (Jan. 17-22, 2000).

Otonkoski, T. et al., "Differentiation and maturation of porcine fetal islet cells in vitro and after transplantation," *Transplantation* 68:1674-83 (1999).

Peck, A. et al., "Pancreatic Stem Cells: Building Blocks for a Better Surrogate Islet to Treat Type 1 Diabetes," *Ann. Med.* 33(3):186-92 (Apr. 2001).

Portela-Gomes, G. & H öög, A., "Insulin-like growth factor II in human fetal pancreas and its co-localization with the major islet hormones: comparison with adult pancreas," *J. Endocrinol.* 165:245-51 (2000).

Rajagopal, J. et al., "Insulin staining of ES cell progeny from insulin uptake," *Science* 299:363 (2001).

Roche, E. et al., "Bio-engineering insulin-secreting cells from embryonic stem cells: a review of progress," *Med. Biol. Eng. Comput.* 41(4):384-391 (2003).

Roep, B. et al., "Auto—and Alloimmune Reactivity to Human Islet Allografts Transplanted into Type 1 Diabetic Patients," *Diabetes* 48:484-90 (Mar. 1999).

Schuldiner, M. et al., "Effects of eight growth factors on the differentiation of cells derived from human embryonic stem cells," *Proc. Natl. Acad. Sci.* 97:11307-12 (2000).

Segev, H. et al., "Differentiation of human embryonic stem cells into insulin-producing clusters," *Stem Cells* 22(3):265-74 (2004).

Shamblott, M. et al., "Derivation of Pluripotent Stem Cells from Cultured Human Primordial Germ Cells," *Proc. Natl. Acad. Sci. USA* 95:13726-31 (Nov. 1998).

Shapiro, A. et al., "Islet transplantation in seven patients with type 1 diabetes mellitus using a glucocorticoid-free immunosuppressive regimen," *N. Engl. J. Med.* 343(4):230-8 (Jul. 2000).

Soria, B. et al., "From stem cells to beta cells: new strategies in cell therapy of diabetes mellitus," *Diabetologia* 44:407-15 (2001).

Soria, B. et al., "Insulin-Secreting Cells Derived from Embrynic Stem Cells Normalize Glycemia in Streptozotocin-Induced Diabetic Mice," *Diabetes* 49(2): 157-62 (Feb. 2000).

Soria, B., "In-Vitro Differentiation of Pancreatic Beta-Cells," *Differentiation* 68(4-5):205-19 (Oct. 2001).

Thomson, J. et al., "Embryonic Stem Cell Lines Derived from Human Blastocysts," *Science* 282:1145-7 (Nov. 1998).

Thomson, J. et al., "Isolation of a primate embryonic stem cell line," *Proc. Natl. Acad. Sci. USA* 92:7844-8 (1995).

Wang, H. et al., "Pdx1 level defines pancreatic gene expression pattern and cell lineage differentiation," *J. Biol. Chem.* 276(27):25279-86 (2001).

Xu, X. et al., "Endoderm and pancreatic islet lineage differentiation from human embryonic stem cells," *Cloning Stem Cells* 8(2):96-107 (2006).

Yamaoka, T. & Itakura, M., "Development of Pancreatic Islets (Review)," *Int. J. Mol. Med.* 3:247-61 (1999).

Yang, L. et al., "In Vitro Trans-Differentiation of Adult Hepatic Stem Cells into Pancreatic Endocrine Hormone-Producing Cells," *Proc. Natl. Acad. Sci.* 99(12):8078-83 (Jun. 2002).

Yoshida, K. & Kikutani, H., "Genetic and Immunological Basis of Autoimmune Diabetes in the NOD Mouse," *Rev. Immuogenetics* 2(1):140-6 (2000).

Zulewski, H. et al., "Muiltipotetial Nestin-Positive Stem Cells Isolated from Adult Pancreatic Islets Differentiate ex Vivo into Pancreatic Endocrine, Exocrine, and Hepatic Phenotypes," *Diabetes* 50(3):521-33 (Mar. 2001).

Blouin, M. et al., "Specialization switch in differentiating embryonic rat liver progenitor cells in response to sodium butyrate", *Exp. Cell Res. 217* (1995), pp. 22-30.

Kosaka, M. et al., "Reversible effects of sodium butyrate on the differentiation of F9 embryonal carcinoma cells", *Exp. Cell Res. 192*(1) (1991), pp. 46-51.

Wiles, M. et al., "Embryonic stem cell development in a chemically defined medium", *Exp. Cell Res. 247* (1999), pp. 241-8.

Beattie, G. et al., "Sustained proliferation of PDX-1+ cells derived from human islets", *Diabetes 48* (1999), pp. 1013-1019.

Duncan, S., "The pancreas and its heartless beginnings", *Nature Genet. 27*(4) (2001), pp. 355-6.

Lebkowski, J. et al., "Differentiation of human embryonic stem cells into hepatocytes, cardiomyocytes and neurons: transplantation applications", *Blood 98*(11) (2001), pp.548-9.

Otonkoski, T. et al., "Nicotinamide is a potent inducer of endocrine differentiation in cultured human fetal pancreatic cells", *J. Clin. Invest. 92*(1993), pp. 1459-1466.

Rabinovitch, A. et al., "Transfection of human pancreatic islets with an anti-apoptotic gene (bcl-2) protects Beta-cells from cytokine induced destruction", *Diabetes 48* (1999), pp. 1223-1229.

Gonzaga-Juaregui, C. et al., "Human genome sequencing in health and disease", *Annu. Rev. Med. 63*,(2012 )pp. 35-61.

Hapmap, "A second generation human haplotype map of over 3.1 million SNPs", *The International HapMap Consortium, Nature 449*, (2007),pp. 851-862.

Pearson, H. "Diabetes therapy called into question", *Nature Online*, (Jan. 17, 2003), 2 pages.

Reubinoff, B. et al., "Embryonic stem cells lines from human blastocysts: somatic differentiation in vitro", *Nat. Biotech. 18*, (2000),pp. 399-404.

Rotimi, C. et al., "Ancestry and disease in the age of genomic medicine", *N. Engl. J. Med. 363*, (2010), pp. 1551-1558.

"Human Genetic Variation", *Wikipedia pages*, (2012), pp. 1-18.

Levy, S. et al., "The diploid genome sequence of an individual human", *PLoS Biol. 5*(10), (2007), pp. 2113-44.

"Breakthrough of 2007—Human Genetic Validation", *Pages printed from The Tech Museum website*, www.thetech.org/genetics/news.php?id=74, (2008), 4 pages.

\* cited by examiner

FACS Analysis of hES-differentiated Insulin-Producing Cells

SEQUENCE LISTING

<160> NUMBER OF SEQ ID NOS: 12

<210> SEQ ID NO 1
<211> LENGTH: 20

```
<212> TYPE: DNA
<213> ORGANISM: Artificial sequence
<220> FEATURE:
<223> OTHER INFORMATION: cDNA primer

<400> SEQUENCE: 1
cctttcccat ggatgaagtc                                          20

<210> SEQ ID NO 2
<211> LENGTH: 20
<212> TYPE: DNA
<213> ORGANISM: Artificial sequence
<220> FEATURE:
<223> OTHER INFORMATION: cDNA primer

<400> SEQUENCE: 2
tctctattct tttgcgccgg                                          20

<210> SEQ ID NO 3
<211> LENGTH: 17
<212> TYPE: DNA
<213> ORGANISM: Artificial sequence
<220> FEATURE:
<223> OTHER INFORMATION: cDNA primer

<400> SEQUENCE: 3
gggaggcaga ggacctg                                             17

<210> SEQ ID NO 4
<211> LENGTH: 20
<212> TYPE: DNA
<213> ORGANISM: Artificial sequence
<220> FEATURE:
<223> OTHER INFORMATION: cDNA primer

<400> SEQUENCE: 4
gctgccaagg aattcattgc                                          20

<210> SEQ ID NO 5
<211> LENGTH: 16
<212> TYPE: DNA
<213> ORGANISM: Artificial sequence
<220> FEATURE:
<223> OTHER INFORMATION: cDNA primer

<400> SEQUENCE: 5
cgtccgttgt ctcctc                                              16

<210> SEQ ID NO 6
<211> LENGTH: 18
<212> TYPE: DNA
<213> ORGANISM: Artificial sequence
<220> FEATURE:
<223> OTHER INFORMATION: cDNA primer

<400> SEQUENCE: 6
cttggacagt gggcgcac                                            18

<210> SEQ ID NO 7
<211> LENGTH: 18
<212> TYPE: DNA
<213> ORGANISM: Artificial sequence
<220> FEATURE:
<223> OTHER INFORMATION: cDNA primer

<400> SEQUENCE: 7
ccacaatgcc acgcttct                                            18
```

```
<210> SEQ ID NO 8
<211> LENGTH: 22
<212> TYPE: DNA
<213> ORGANISM: Artificial sequence
<220> FEATURE:
<223> OTHER INFORMATION: cDNA primer

<400> SEQUENCE: 8
cttcaacaat ggcgacctct tc                                              22

<210> SEQ ID NO 9
<211> LENGTH: 21
<212> TYPE: DNA
<213> ORGANISM: Artificial sequence
<220> FEATURE:
<223> OTHER INFORMATION: cDNA probe

<400> SEQUENCE: 9
aagctcacgc gtggaaaggc c                                               21

<210> SEQ ID NO 10
<211> LENGTH: 25
<212> TYPE: DNA
<213> ORGANISM: Artificial sequence
<220> FEATURE:
<223> OTHER INFORMATION: cDNA probe

<400> SEQUENCE: 10
agaaaggatg acgcctcaac cctcg                                           25

<210> SEQ ID NO 11
<211> LENGTH: 20
<212> TYPE: DNA
<213> ORGANISM: Artificial sequence
<220> FEATURE:
<223> OTHER INFORMATION: cDNA probe

<400> SEQUENCE: 11
aggtggggca ggtggagctg                                                 20

<210> SEQ ID NO 12
<211> LENGTH: 24
<212> TYPE: DNA
<213> ORGANISM: Artificial sequence
<220> FEATURE:
<223> OTHER INFORMATION: cDNA probe

<400> SEQUENCE: 12
tgaaaggccg aggaaggcga gatt                                            24
```

DIFFERENTIATION AND ENRICHMENT OF ISLET-LIKE CELLS FROM HUMAN PLURIPOTENT STEM CELLS

PRIORITY

This application claims priority to Intl. Appl. No. PCT/U.S.07/012,489, filed May 25, 2007, and provisional Appl. No. 60/815,111, filed Jun. 19, 2006.

FIELD OF THE INVENTION

This invention relates to the field of in-vitro differentiation of human pluripotent stem cells islet-like cells, which include insulin-producing cells. The invention also relates to the field of enrichment of human pluripotent stem cell-derived islet-like cells.

BACKGROUND

The American Diabetes Association estimates that there are currently 5 million people in the United States with confirmed diabetes, and over 10 million at risk. Care of diabetics consumes a total of $98 billion per year, accounting for one of every seven healthcare dollars spent in the U.S. There are 24,000 new cases of diabetes-caused blindness caused by diabetes each year. Diabetes is the leading cause of kidney failure, contributing about 40% of new dialysis patients. Diabetes is also the most frequent cause of lower limb amputation, with 56,000 limbs lost to diabetes each year. Type I diabetes mellitus (also known as insulin-dependent diabetes) is a severe condition accounting for 5-10% all diabetics.

There are several clinical tests underway to transplant diabetics with islet cells isolated from donor pancreas. This has been made possible by recent advances in the isolation and transplantation of islet cells. For example, the Edmonton Protocol was developed in the 1990's, and over 200 people have received cadaveric islet transplants using that protocol.

However, the supply of islet cells from cadaveric donors limits the application of islet transplants as a large-scale therapy. Thus, the development of methods for differentiating and purifying islet cells from a renewable source such as embryonic stem cells is an important goal. For embryonic stem cell derived islet cells to become a commercially viable proposition, there is a need to develop new procedures that provide for populations of islet cells of high purity.

SUMMARY OF THE INVENTION

The invention provides, inter alia, methods of enriching the proportion of islet-like cells from a cell population generated by the differentiation of human pluripotent stem cells to islet-like cells, comprising differentiating human pluripotent stem cells to a cell population comprising islet-like cells, wherein the cell population comprises cell clusters that have formed buds; and separating at least some of the buds from at least some of the clusters in the cell population into at least two fractions; wherein at least one of the at least two resulting fractions contains a higher proportion of islet-like cells than the cell population. In certain embodiments, the islet-like cells are insulin-producing cells. In certain embodiments, the islet-like cells are glucagon-producing cells. In certain embodiments, the human pluripotent stem cells are human embryonic stem cells.

In certain embodiments, the buds are separated from the clusters based on size differences between the buds and the clusters. In certain of those embodiments, the buds are separated from the clusters by use of nylon mesh. The nylon mesh may be a 200 micron mesh or a 70 micron mesh. The nylon mesh may be between 50 and 250 microns.

In certain embodiments using a size separation step, at least one of the fractions with a higher proportion of islet-like cells than the cell population is a fraction with a smaller particle size than at least one of the other fractions that result from the size separation. In certain of those embodiments, the at least one fraction with a higher proportion of islet-like cells than the cell population has a particle size equal to or less than 200 microns. In certain embodiments, the at least one fraction with a higher proportion of islet-like cells than the cell population has a particle size equal to or less than 150 microns. In certain embodiments, the at least one fraction with a higher proportion of islet-like cells than the cell population has a particle size equal to or less than 100 microns.

In certain embodiments using size separation, the cell population is fractionated into three fractions by performing two size separation steps, wherein the second separation step is performed on a fraction that results from the first separation step. In certain of those embodiments, the first separation step is performed using a size separation value equal to or less than 50 microns and the second separation step is performed using a size separation value between 100 microns and 300 microns on the retained fraction from the first separation step; wherein the pass-through fraction from the second separation step contains a higher proportion of islet-like cells than the cell population. In certain of those embodiments, the first separation step is performed using a size separation value of 50 microns and the second separation step is performed using a size separation value of 150 microns, wherein the resulting 50 to 150 micron fraction contains higher proportion of islet-like cells than the cell population.

In certain embodiments using size separation, the first separation step is performed using a size separation value equal to or less than 50 microns and the second separation step is performed using a size separation value between 150 microns and 250 microns on the retained fraction from the first separation step; wherein the pass-through fraction from the second separation step contains a higher proportion of islet-like cells than the cell population. In certain of those embodiments, the first separation step is performed using a size separation value of 50 microns and the second separation step is performed using a size separation value of 200 microns, wherein the 50 to 200 micron fraction contains higher proportion of islet-like cells than the cell population.

In certain embodiments using size separation, the first separation step is performed using a size separation value equal to or less than 20 microns and the second separation step is performed using a size separation value of 100 microns or greater on the retained fraction from the first separation step; wherein the pass-through fraction from the second separation step contains a higher proportion of islet-like cells than the cell population. In certain of those embodiments, the first separation step is performed using a size separation value of 20 microns and the second separation step is performed using a size separation value of 200 microns, wherein the resulting 20 to 200 micron fraction contains higher proportion of islet-like cells than the cell population.

In certain embodiments, the buds are dissociated from the clusters before the separation step. In certain of those embodiments, the buds are dissociated from the clusters by repeated pipetting. In certain of those embodiments, the buds are dissociated from the clusters by enzyme treatment. In certain embodiments, the enzyme used for dissociation of buds and clusters is Dispase. In certain embodiments, the enzyme used for dissociation of buds and clusters is trypsin, Benzyme, or proteinase XXIII.

In certain embodiments of the enrichment, the buds are separated from the clusters by manually or robotically picking the buds. In certain embodiments of the enrichment, the buds are separated from at least some of the clusters using flow cytometry based on the relative size differences.

In certain embodiments of the enrichment, the buds are separated from the clusters based on density differences between the buds and the clusters. In certain of those embodiments, the buds are separated from at least some of the clusters using differential centrifugation. In certain of those embodiments, the differential centrifugation is done using a gradient. In certain of those embodiments, the gradient is a Percoll gradient.

DESCRIPTION OF THE FIGURES

FIG. 2A shows the isotype control staining; and FIG. 2B shows staining with the anti human C-peptide antibody.

DETAILED DESCRIPTION

Definitions

Figure 1:
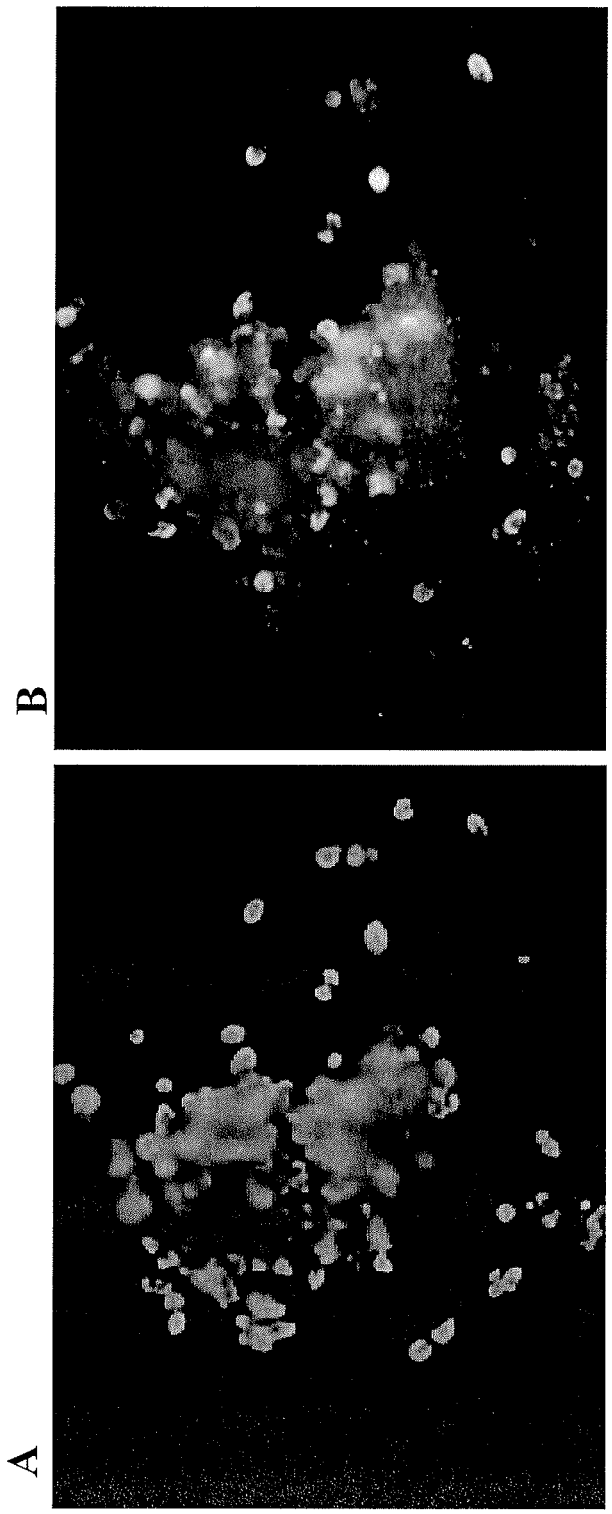
FIG. 1—Colocalization of C-peptide (A) and glucagon (B) in the cell population at day 36 of a differentiation of human embryonic stem cells to islet-like cells. The cell population was first incubated with 2 ug/ml murine anti-human C-peptide (Monosan catalog #MON5021) and 2 ug/ml Rabbit anti-glucagon (Chemicon catalog #AB932) and then visualized using two secondary antibodies—Fluro Alexa 594-labelled goat anti-mouse IgG and Fluro Alexa 488-labelled goat anti-rabbit IgG.

The term "particle size" as used herein refers to the size of the particles that pass through a filter with a certain given average pore size or that are not able to pass through a filter with a certain given average pore size. In certain embodiments, a particle is a single cell or is an aggregate of multiple cells.

For example, if a cell population is filtered through a 200 micron mesh, the particles that pass through the mesh are said to have a particle size of equal to or less than 200 microns, while the particles that are retained by the mesh are said to have a particle size of greater than 200 microns. However, designating a fraction as having less than a certain particle size does not mean that the fraction is devoid of any particles with a size greater than that particle size as the mesh may allow a few particles with a size greater than the particle size of the mesh to pass through. Conversely, the mesh may also retain a few particles with a size less than the particle size of the mesh.

The term "size separation value" as used herein refers to size at which a filter or other size separation method fractionates a population of particles. For example, a 200 micron mesh has a size separation value of 200 microns and will fractionate a population of particles into a fraction of particles with sizes equal to or less than 200 microns and a population of particles with sizes over 200 microns. However, the fractionation is not required to be complete; for example, certain particles with sizes over 200 micron may pass through the mesh into the equal to or less than 200 micron fraction.

The term "islet-like cells" refers cells that produce at least one of the endocrine markers characteristic of β-islets of the pancreas. Those endocrine markers are insulin, glucagon, somatostatin, and pancreatic polypeptide.

The term "insulin-producing cells" refers to cells that produce insulin. Insulin production can be determined either at the mRNA level or the protein level. The production of C-peptide may be used to indicate that a cell produces insulin.

The term "glucagon-producing cells" refers to cells that produce glucagon. Glucagon production can be determined either at the mRNA level or the protein level.

As used herein, "bud" refers to an outgrowth of cells that forms on the cell clusters that arise during a differentiation of human pluripotent stem cells into islet-like cells.

As used herein, "cluster" refers to an aggregate of cells that form during a differentiation of human pluripotent stem cells to islet-like cells.

The term, "embryoid bodies" refers to heterogeneous cellular aggregates comprising differentiated and partly differentiated cells that appear when human pluripotent stem cells are allowed to differentiate in a non-specific fashion in suspension cultures or monolayer cultures.

As used herein, "human pluripotent stem cells" or "hPs cells" refer to cells that are capable of producing cell types that are derivatives of all of the 3 germinal layers (endoderm, mesoderm, and ectoderm). One exemplary test is the ability to form teratomas in 8-12 week old SCID mice. See, e.g., Przyborski, S. A., *Stem Cells* 23:1242-50 (2005).

Included in the definition of human pluripotent stem cells are embryonic cells of various types, exemplified by, but not limited to, human embryonic stem (hES) cells, (see, e.g., Thomson et al. (Science 282:1145, 1998)) and human embryonic germ (hEG) cells (see, e.g., Shamblott et al., Proc. Natl. Acad. Sci. USA 95:13726, 1998).

As used herein, "human embryonic stem cells" or "hES cells" refers to pluripotent stem cells that are derived from a human embryo at the blastocyst stage, or the pluripotent progeny thereof. Certain "human Embryonic Stem cells" (hES cells) are described by Thomson et al. (Science 282: 1145, 1998; U.S. Pat. No. 6,200,806; Curr. Top. Dev. Biol. 38:133 ff., 1998) and Reubinoff et al. (Nature Biotech. 18:399, 2000).

As used herein, "direct differentiation" refers to a process for differentiating human pluripotent stem cells into progeny that are enriched for cells of a particular lineage without forming embryoid bodies as an intermediate. The term direct differentiation encompasses processes in which a small number of cell aggregates form inadvertently.

As used herein, "genetically altered," "transfected," or "genetically transformed" refer to a process where a polynucleotide has been transferred into a cell by any suitable means of artificial manipulation, or where the cell is a progeny of the originally altered cell and has inherited all or part of the polynucleotide. The polynucleotide may comprise a transcribable sequence encoding a protein of interest, which enables the cell to express the protein. In certain embodiments, the polynucleotide comprises a sequence encoding a molecule such as siRNA or antisense RNA that affects the expression of a protein (either an endogenous protein or an exogenous protein, e.g., that is expressed as the result of the introduction of a polynucleotide sequence). The genetic alteration is said to be "inheritable" if progeny of the altered cell have the same alteration.

As used herein, "serum-free" refers to a condition where the referenced composition contains no added serum.

As used herein, "feeder-free" refers to a condition where the referenced composition contains no added feeder cells. The term feeder-free encompasses, inter alia, situations where human pluripotent stem cells are passaged from a culture with feeders into a culture without added feeders even if some of the feeders from the first culture are present in the second culture. The term feeder-free also encompasses situations where some of the cultured human pluripotent stem cells have themselves differentiated into feeder cells.

Expression of an antigen by a cell is said to be "antibody-detectable" if the antibody will bind to the antigen in a standard immunocytochemistry or flow cytometry assay, optionally after fixing the cells, at a level that is at least 2-fold above the background level of binding by a control antibody. In various embodiments, the level of antibody binding is at least 5 fold or at least 10 fold above the background level of binding by the control antibody. Control antibodies include, but are not limited to, antibodies to antigens that are predicted not to be present in the selected cell population.

DETAILED DESCRIPTION OF CERTAIN EMBODIMENTS

Methods for producing and enriching islet-like cells from human pluripotent stem cells are provided herein. Furthermore, it has been discovered that, due to the formation of buds on the differentiating clusters, fractionating buds from clusters in a population of cells differentiated from human pluripotent stem cells results in a significant enrichment in the proportion of islet-like cells in the fraction enriched for the buds. In particular, it was discovered that the fractionation of buds from clusters results in a significant enrichment in the proportion of insulin- and glucagon-producing cells.

For example, one approach to separating the buds from the clusters is based on the size difference between the buds and the clusters as the buds are smaller than the clusters. In certain embodiments, the cell population is fractionated into two fractions using a filter or mesh with a separation value between 100 and 300 microns. In certain of those embodiments, a nylon mesh may be used to separate the differentiated cell population into three fractions with particle sizes equal to or less than 70 microns, between 70 and 200 microns, and greater than 200 microns, resulting in two fractions enriched for islet-like cells—the equal to or less than 70 micron fraction and the 70 to 200 micron fraction. The invention, however, is not limited to using 70 micron and 200 micron mesh for size separations. Nor is the invention limited to separating buds from clusters by size. Other methods for separating buds from clusters, such as differential centrifugation, are also discussed below.

General Techniques

For further elaboration of general techniques useful in the practice of this invention, one skilled in the art can refer to standard textbooks and reviews, for example, in the fields of cell biology, tissue culture, embryology, and cardiophysiology.

With respect to tissue and cell culture and embryonic stem cells, one skilled in the art may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998; and R. I. Freshney, Culture of Animal Cells, Wiley-Liss, New York, 2000). General methods in molecular and cellular biochemistry can be found in standard textbooks, including but not limited to, *Short Protocols in Molecular Biology*, 4$^{th}$ Ed.; *Immunology Methods Manual* (I. Lefkovits ed., Academic Press 1997); and *Cell and Tissue Culture: Laboratory Procedures in Biotechnology* (Doyle & Griffiths, John Wiley & Sons 1998).

Certain Exemplary Reagents

As used herein, "Activin" refers to a primate polypeptide growth factor comprising at least one of Activin A, Activin B, Activin C, an active fragment of any of those Activins, and/or an active protein that is at least 95% identical to Activin A, Activin B, and/or Activin C. In certain embodiments, an Activin is a human, primate, or mouse Activin.

As used herein, "Activin peptide" refers to a primate polypeptide growth factor comprising at least one of Activin A, Activin B, Activin C, and/or an active fragment of any of those Activins. In certain embodiments, Activin is a dimer selected from an Activin A homodimer, an Activin B homodimer, an Activin AB heterodimer, an Activin C homodimer. In certain embodiments, Activin is selected from one of the aforementioned dimers in which one or both polypeptides is an active fragment of Activin A, B, or C. In certain embodiments, an Activin peptide is a human, primate, or mouse Activin peptide.

A fragment of Activin A, Activin B, or Activin C, or a protein that is at least 95% identical to Activin A, Activin B, and/or Activin C is considered to be active if cells that produce insulin are produced when the protocol described in Example 1 is carried out, but with the Activin A in the protocol replaced with the fragment of Activin A, Activin B, or Activin C, and/or the protein that is at least 95% identical to Activin A, Activin B, and/or Activin C being tested.

As used herein, "EGF" refers to an epidermal growth factor. In certain embodiments, an EGF is a human, primate, or mouse EGF. As used herein, "EGF polypeptide" refers to EGF, an active fragment of EGF, and/or an active protein that is at least 95% identical to EGF. A human EGF polypeptide refers to human EGF, an active fragment of human EGF, and/or an active protein that is at least 95% identical to human EGF.

A fragment of an EGF, or a protein that is at least 95% identical to an EGF is considered to be active if cells that produce insulin are produced when the protocol described in Example 1 is carried out, but with the EGF in the protocol replaced with the fragment of an EGF, or the protein that is at least 95% identical to an EGF being tested.

As used herein, "bFGF" or "FGF-2" refers to a basic fibroblast growth factor. In certain embodiments, a bFGF is a human, primate, or mouse bFGF. As used herein, "bFGF polypeptide" or "FGF2 polypeptide" refers to a bFGF, an active fragment of a bFGF, and/or an active protein that is at least 95% identical to a bFGF. A human bFGF polypeptide refers to a human bFGF, an active fragment of human bFGF, and/or an active protein that is at least 95% identical to a human bFGF.

A fragment of a bFGF, or a protein that is at least 95% identical to a bFGF is considered to be active if cells that produce insulin are produced when the protocol described in Example 1 is carried out, but with the bFGF in the protocol replaced with the fragment of a bFGF, or the protein that is at least 95% identical to a bFGF being tested.

As used herein, "IGF-II" refers to insulin growth factor 2. In certain embodiments, IGF-II is a human, primate, or mouse IGF-II. As used herein, "IGF-II polypeptide" refers to an IGF-II, an active fragment of IGF-II, and/or an active protein that is at least 95% identical to an IGF-II. A human IGF-II polypeptide refers to human IGF-II, an active fragment of human IGF-II, and/or an active protein that is at least 95% identical to human IGF-II.

A fragment of a IGF-II, or a protein that is at least 95% identical to IGF-II is considered to be active if cells that produce insulin are produced when the protocol described in Example 1 is carried out, but with the IGF-II in the protocol replaced with the fragment of IGF-II, or the protein that is at least 95% identical to IGF-II being tested.

As used herein, "noggin" refers to the factor noggin. In certain embodiments, noggin is a human, primate, or mouse noggin As used herein, "noggin polypeptide" refers to a noggin, an active fragment of a noggin, and/or an active protein that is at least 95% identical to a noggin. A human noggin polypeptide refers to a human noggin, an active fragment of human noggin, and/or an active protein that is at least 95% identical to a human noggin.

A fragment of a noggin, or a protein that is at least 95% identical to a noggin is considered to be active if cells that produce insulin are produced when the protocol described in Example 1 is carried out, but with the noggin in the protocol replaced with the fragment of a noggin, or the protein that is at least 95% identical to a noggin being tested.

As used herein, "nicotinamide" refers to pyridine-3-carboxamide.

As used herein, "sodium butyrate" refers to a chemical having the formula $CH_3CH_2CH_2COONa$.

As used herein, "BSA" refers to a bovine serum albumin.

As used herein, the "culture medium" refers to liquid media used to culture and differentiate human pluripotent stem cells. Exemplary culture media are based on basic media including, but are not limited to, RPMI-1640 (Invitrogen (Gibco) Catalog #11875-093), Knockout DMEM (GibcoBRL/Invitrogen cat no. 10829-018), and HCM Bullet Kit (Cambrex/Clonetics/Biowhittaker Catalog #CC-3198). In certain embodiments, one or more supplements are added to the basic media to form the culture media. Exemplary supplements that may be included in the culture media for one or more periods of time during the methods described herein include, but are not limited to, B27 (GibcoBRL/Invitrogen Catalog #17504-044), B27 Supplement without vitamin A (e.g., GibcoBRL/Invitrogen Catalog #12587-010), N2 supplement (GibcoBRL/Invitrogen Catalog #17502-048), and G5 supplement (GibcoBRL/Invitrogen Catalog #17503-012), L-glutamine (e.g., 200 mM solution, GibcoBRL/Invitrogen Catalog #25030-81), non-essential amino acids (e.g., GibcoBRL/Invitrogen Catalog #11140-050), and β-mercaptoethanol (e.g., Sigma Catalog #M7522).

As used herein "serum replacement" refers to a composition added to the culture media that mimics serum, but is not derived from animal products. Exemplary serum replacements include, but are not limited to, Knockout™ Serum Replacement (GibcoBRL/Invitrogen cat. no. 10828-028).

As used herein, "basement membrane matrix" or "extracellular matrix" refers to a composition used in vitro to mimic the in vivo mammalian cellular basement membrane. Exemplary basement membrane matrices include, but are not limited to, BD Matrigel Basement Membrane Matrix (Becton, Dickinson Co., Franklin Lakes, N.J.) ("Matrigel"). In certain embodiments, a basement membrane matrix comprises one or more of laminin, collagen IV, heparan sulfate proteoglycans, and entactin. In certain embodiment, a basement membrane matrix is derived from Engelbreth-Holm-Swarm tumor cells.

As used herein, "feeder cells" refers to cells of a first tissue type that may act to promote proliferation and/or control differentiation of cells of a second tissue type when the cells are cocultured together. In certain embodiments, the feeder cells are of a different cell type than the cocultured cells. For example, human pluripotent stem cells can be cocultured with embryonic fibroblasts of the same or different species. In various embodiments, feeder cells may help maintain the undifferentiated state of human pluripotent stem cells or may help direct differentiation towards a particular tissue type (e.g., islet-like cells). In certain embodiments, feeder cells may be differentiated from human pluripotent stem cells. See, e.g., WO 01/51616.

Human Pluripotent Stem Cells

Methods for differentiating human pluripotent stem cells into islet-like cells are provided. Human pluripotent stem cells that may be used in the methods include, but are not limited to, embryonic stem cells. Embryonic stem cells can be isolated, e.g., from blastocysts of human species (see, e.g., U.S. Pat. No. 5,843,780; Thomson et al., Proc. Natl. Acad. Sci. USA 92:7844, 1995). Human embryonic stem (hES) cells can be prepared, e.g., from human blastocyst cells using, for example, the techniques described by Thomson et al. (U.S. Pat. No. 6,200,806; Science 282:1145, 1998; Curr. Top. Dev. Biol. 38:133 ff., 1998) and Reubinoff et al. (Nature Biotech. 18:399, 2000). Certain other human pluripotent stem cell types include, but are not limited to, primitive ectoderm-like (EPL) cells (see, e.g., WO 01/51610 (Bresagen)) and human embryonic germ (hEG) cells (see, e.g., Shamblott et al., Proc. Natl. Acad. Sci. USA 95:13726, 1998).

Embryonic stem cells may be chosen from embryonic stem cell lines or may be obtained directly from primary embryonic tissue. A number of embryonic stem cell lines have been established including, but not limited to, H1, H7, H9, H13 and H14 (Thompson et al.); hESBGN-01, hESBGN-02, hES-BGN-03 (BresaGen, Inc., Athens, Ga.); HES-1, HES-2, HES-3, HES-4, HES-5, HES-6 (ES Cell International, Inc., Singapore); HSF-1, HSF-6 (University of California at San Francisco); 13, 14, 16 (Technion-Israel Institute of Technology, Haifa, Israel); UCSF-1 and UCSF-2 (Genbacev et al., Fertil. Steril. 83(5):1517-29, 2005); lines HUES 1-17 (Cowan et al., NEJM 350(13):1353-56, 2004); and line ACT-14 (Klimanskaya et al., Lancet, 365(9471):1636-41, 2005).

In certain embodiments, human pluripotent stem cells may have been derived in a feeder-free manner (see, e.g., Klimanskaya et al., Lancet, 365(9471):1636-41 (2005)).

Human Pluripotent Stem Cell Culture

Human pluripotent stem cells may be cultured using a variety of substrates, media, and other supplements and factors known in the art. Human pluripotent stem cells can be propagated continuously in culture, using culture conditions that promote proliferation while inhibiting differentiation. Exemplary media include 80% DMEM (such as Knock-Out DMEM, GibcoBRL), 20% of either defined fetal bovine serum (FBS, Hyclone) or serum replacement (US 2002/0076747 A1, Life Technologies Inc.), 1% non-essential amino acids, 1 mM L-glutamine, 0.1 mM β-mercaptoethanol, and 4 ng/ml bFGF (GibcoBRL/Invitrogen). The media is conditioned by overnight culture with mitotically inactivated mouse embryonic fibroblasts. An additional 8 ng/ml bFGF was added to the media before it was used for pluripotent stem cell culture.

In certain embodiments, human pluripotent stem cells are cultured on a layer of feeder cells, typically fibroblasts derived from embryonic or fetal tissue (see, e.g., Thomson et al., Science 282:1145, 1998). In certain embodiments, those feeder cells are of human or mouse origin. Human feeder cells can be isolated from various human tissues or derived by differentiation of human embryonic stem cells into fibroblast cells (see, e.g., WO 01/51616). In certain embodiments, human feeder cells include, but are not limited to, placental fibroblasts (see, e.g., Genbacev et al., Fertil. Steril. 83(5): 1517-29, 2005), fallopian tube epithelial cells (see, e.g., Richards et al., Nat. Biotechnol., 20:933-36, 2002), foreskin fibroblasts (see, e.g., Amit et al., Biol. Reprod. 68:2150-56, 2003), and uterine endometrial cells (see, e.g., Lee et al., Biol. Reprod. 72(1):42-49, 2005).

In certain embodiments, human pluripotent stem cells may be maintained in an undifferentiated state without added feeder cells (see, e.g., Rosler et al., Dev. Dyn. 229:259-274, 2004). Feeder-free cultures are typically supported by a nutrient medium containing factors that promote proliferation of the cells without differentiation (see, e.g., U.S. Pat. No. 6,800, 480). In certain embodiments, such factors may be introduced into the medium by culturing the medium with cells secreting such factors, such as irradiated (~4,000 rad) primary mouse embryonic fibroblasts, telomerized mouse fibroblasts, or fibroblast-like cells derived from human pluripotent stem cells (see, e.g., U.S. Pat. No. 6,642,048). Medium can be conditioned, e.g., by plating the feeders in a serum free medium such as KO DMEM supplemented with 20% serum replacement and 4 ng/mL bFGF. Medium that has been conditioned for 1-2 days is supplemented with further bFGF, and used to support human pluripotent stem cell culture for 1-2 days (see. e.g., WO 01/51616; Xu et al., Nat. Biotechnol. 19:971, 2001).

Alternatively, fresh or non-conditioned medium can be used, which has been supplemented with added factors (such as, for example, fibroblast growth factor and/or forskolin) that promote proliferation of the cells in an undifferentiated form. An exemplary non-conditioned medium includes a base medium like X-VIVO 10 (Biowhittaker) or QBSF-60 (Quality Biological Inc.), supplemented with bFGF at 40-100 ng/mL, and optionally containing stem cell factor (15 ng/mL), noggin (0.5 µg/mL), or Flt3 ligand (75 ng/mL) (see, e.g., Xu et al., Stem Cells 23(3):315-23, 2005; Xu et al., Nature Methods 2(3): 185-90 (2005)). These medium formulations have the advantage of supporting cell growth at 2-3 times the rate of other systems (see, e.g., WO 03/020920).

Certain nonlimiting exemplary pluripotent stem cell culture methods follow. The human pluripotent stem cells are plated at >15,000 cells cm$^{-2}$ (for example, 90,000 cm$^{-2}$ to 170,000 cm$^{-2}$). Enzymatic digestion, e.g., with trypsin, may be halted before cells become completely dispersed (e.g., ~5 min with collagenase IV). Clumps of ~10 to 2,000 cells may be plated directly onto the substrate without further dispersal. Alternatively, the cells may be harvested without enzymes before the plate reaches confluence by incubating ~5 min in a solution of 0.5 mM EDTA in PBS or by simply detaching the desired cells from the plate mechanically, such as by scraping or isolation with a fine pipette. After washing from the culture vessel, the cells may be plated into a new culture without further dispersal. In a further illustration, confluent human embryonic stem cells cultured in the absence of feeders may be removed from the plates by incubating with a solution of 0.05% (wt/vol) trypsin (Gibco) and 0.053 mM EDTA for 5-15 min at 37° C. The remaining cells in the plate are removed and the cells are triturated into a suspension comprising single cells and small clusters, and then plated at densities of 50,000-200,000 cells cm$^{-2}$.

Under the microscope, human pluripotent stem cells appear with high nuclear/cytoplasmic ratios, prominent nucleoli, and compact colony formation with poorly discernable cell junctions. Primate pluripotent stem cells may express certain stage-specific embryonic antigens, including, but not limited to, SSEA 3, and SSEA 4, and certain markers detectable using antibodies designated Tra-1-60 and Tra-1-81. In certain embodiments, human embryonic stem cells express the transcription factor Oct-3/4, Cripto, gastrin-releasing peptide (GRP) receptor, podocalyxin-like protein (PODXL), and human telomerase reverse transcriptase (hTERT) (see, e.g., US 2003/0224411 A1), as detected by RT-PCR.

Differentiation of Islet-Like Cells from Human Pluripotent Stem Cells

The current invention provides methods for differentiating human pluripotent stem (hPS) cells into islet-like cells, which includes insulin-producing cells and glucagon-producing cells. In certain embodiments of the invention, the methods comprise multiple culturing steps, wherein the first culturing step takes place in the presence of an Activin, the next culturing step utilizes a suspension culture that takes place in the presence of a noggin, an FGF-2, and an EGF, and a final culturing step in which the cells are cultured with nicotinamide.

In certain embodiments, the protocol is as follows. Human embryonic stem cells are first cultured for one week with Activin A and sodium butyrate. The cells are then cultured in suspension for two weeks in a medium comprising noggin, FGF-2, and EGF. For the fourth week, the cells are cultured in suspension in a medium comprising noggin and EGF without FGF-2. For days 29-33, the cells are cultured in suspension in a medium comprising Bovine Serum Albumin ("BSA"), nicotinamide, and IGF-II. For days 34-36, the cells are cultured in suspension in a medium comprising BSA and nicotinamide without IGF-II.

In certain embodiments, the differentiation is performed as in Example 1. In certain other embodiments, the protocol is as described in Example 1 except that B27 without insulin (Invitrogen/Gibco Catalog #005-0129SA) is used in place of the BSA in Culture Medium F and Culture Medium G.

In certain embodiments, at least one Activin is included in the culture medium for between 1 and 21 days, or between 5 and 10 days, or between 6 and 9 days. In certain embodiments, at least one Activin is included in the culture medium for 8 days. In certain embodiments, a first concentration of one or more Activins is included in the culture medium for a first period of time and a second concentration of one or more Activins is included in the culture medium for a second period of time.

In certain embodiments, at least one Activin is included in the culture medium at a concentration between 1 ng/ml and 200 ng/ml, or between 10 ng/ml and 100 ng/ml, or between 25 ng/ml and 100 ng/ml. As a nonlimiting example, 50 ng/ml total concentration of one or more Activins may be included in the culture medium for a total of eight days, although other components may be added, removed, or changed in concentration at any point or points during that time. In certain embodiments, 50 ng/ml of Activin A is included in the culture medium.

In certain embodiments, at least one Activins used in the differentiation comprises an Activin selected from Activin A, Activin B, Activin AB, and Activin C. In certain embodiments, one Activin is used in the differentiation method. In certain embodiments, more than one Activin is used.

In certain embodiments, sodium butyrate is included in the culture medium for between 1 and 21 days, or between 5 and 10 days, or between 6 and 9 days. In certain embodiments, sodium butyrate is included in the culture medium for 8 days. In certain embodiments, a first concentration of sodium butyrate is included in the culture medium for a first period of time and a second concentration of sodium butyrate is included in the culture medium for a second period of time.

In certain embodiments, sodium butyrate is included in the culture medium at a concentration between 0.1 mM and 20 mM, or between 0.2 mM and 5 mM, or between 0.5 mM and 2 mM. As a nonlimiting example, 1 mM sodium butyrate may be included in the culture medium for one day, and then 0.5 mM sodium butyrate may be included in the culture medium for two days. Other components may be added, removed, or changed in concentration at any point or points during that time. In certain embodiments, Activin and sodium butyrate are included in the culture medium at the same time, although each may also be included without the other at one or more times during the same culture protocol.

In certain embodiments, noggin is included in the culture medium for between 5 and 25 days, or between 10 and 20 days, or between 12 and 18 days. In certain embodiments, noggin is included in the culture medium for 14 days. In certain embodiments, a first concentration of noggin is included in the culture medium for a first period of time and a second concentration of noggin is included in the culture medium for a second period of time.

In certain embodiments, noggin is included in the culture medium at a concentration between 1 and 500 ng/ml, between 10 and 200 ng/ml, or between 50 and 150 ng/ml. In certain embodiments, noggin is included in the culture medium at a concentration of 100 ng/ml. As a nonlimiting example, 100 ng/ml noggin may be included in the culture medium for a total of 14 days, although other components may be added, removed, or changed in concentration at any point or points during that time.

In certain embodiments, EGF is included in the culture medium for between 5 and 25 days, or between 10 and 20 days, or between 12 and 18 days. In certain embodiments, EGF is included in the culture medium for 14 days. In certain embodiments, a first concentration of EGF is included in the culture medium for a first period of time and a second concentration of EGF is included in the culture medium for a second period of time. In certain embodiments, the EGF is included in the culture medium with noggin. In certain embodiments, the EGF is included in the culture medium with noggin and FGF-2. In certain embodiments, the EGF is included in the culture medium separately from noggin and FGF-2.

In certain embodiments, EGF is included in the culture medium at a concentration between 1 ng/ml and 100 ng/ml, or between 5 ng/ml and 50 ng/ml, or between 10 ng/ml and 30 ng/ml. As a nonlimiting example, 20 ng/ml EGF may be included in the culture medium for a total of 14 days, although other components may be added, removed, or changed in concentration at any point or points during that time.

In certain embodiments, FGF-2 is included in the culture medium for between 5 and 25 days, or between 10 and 20 days, or between 12 and 18 days. In certain embodiments, FGF-2 is included in the culture medium for 14 days. In certain embodiments, a first concentration of FGF-2 is included in the culture medium for a first period of time and a second concentration of FGF-2 is included in the culture medium for a second period of time. In certain embodiments, the FGF-2 is included in the culture medium with noggin. In certain embodiments, the FGF-2 is included in the culture medium with noggin and EGF. In certain embodiments, the FGF-2 is included in the culture medium separately from noggin and EGF.

In certain embodiments, FGF-2 is included in the culture medium at a concentration between 0.1 mM and 100 mM, or between 0.5 mM and 50 mM, or between 1 mM and 10 mM. As a nonlimiting example, 2 mM FGF-2 may be included in the culture medium for a total of 14 days, although other components may be added, removed, or changed in concentration at any point or points during that time.

In certain embodiments, EGF and FGF-2 are included in the culture medium at the same time, although each may also be included without the other at one or more times during the same culture protocol. In certain embodiments, EGF or FGF-2 are included in the culture medium without the other during part of the differentiation protocol. In certain embodiments, EGF and noggin are included in the culture medium together without FGF-2 for at least part of the differentiation. In certain embodiments, noggin, EGF, and FGF-2 are included together for part of the differentiation protocol, while they are included in the culture medium separately in other parts of the differentiation protocol. In certain embodiments, noggin, EGF, and FGF-2 are included in the culture medium together for part of the differentiation protocol, while noggin and EGF are included together without FGF-2 in another part of the differentiation protocol.

In certain embodiments, nicotinamide is included in the culture medium for between 1 and 20 days, or between 3 and 15 days, or between 5 and 10 days. In certain embodiments, nicotinamide is included in the culture medium for 7 days. In certain embodiments, nicotinamide is included in the culture medium for 7 days. In certain embodiments, a first concentration of nicotinamide is included in the culture medium for a first period of time and a second concentration of nicotinamide is included in the culture medium for a second period of time. In certain embodiments, the nicotinamide is included in the culture medium with BSA and IGF-II. In certain embodiments, the nicotinamide is included in the culture medium separately from noggin and EGF.

In certain embodiments, nicotinamide is included in the culture medium at a concentration between 0.1 mM and 500 mM, or between 0.5 mM and 200 mM, or between 1 mM and 100 mM, or between 5 and 20 mM. As a nonlimiting example, 10 mM nicotinamide may be included in the culture medium for a total of 7 days, although other components may be added, removed, or change concentrations at any point or points during that time.

In certain embodiments, IGF-II is included in the culture medium for between 1 and 20 days, or between 3 and 15 days, or between 5 and 10 days. In certain embodiments, IGF-II is included in the culture medium for 7 days. In certain embodiments, a first concentration of IGF-II is included in the culture medium for a first period of time and a second concentration of IGF-II is included in the culture medium for a second period of time. In certain embodiments, the IGF-II is included in the culture medium with BSA and nicotinamide. In certain embodiments, the IGF-II is included in the culture medium separately from BSA and nicotinamide.

In certain embodiments, IGF-II is included in the culture medium at a concentration between 1 ng/ml and 500 ng/ml, or between 5 ng/ml and 200 ng/ml, or between 10 and 100 ng/ml, or between 20 and 80 ng/ml. As a nonlimiting example, 50 ng/ml IGF-II may be included in the culture medium for a total of 7 days, although other components may be added, removed, or change concentrations at any point or points during that time.

In certain embodiments, the human pluripotent stem cells may be differentiated into islet-like cells by direct differentiation. Differentiation paradigms for human pluripotent stem cells traditionally involve the deliberate formation of embryoid bodies, which allows cross-talk between different cell types, which may promote tissue formation in a manner reminiscent of an embryo. However, it is often advantageous to eliminate the need to form embryoid bodies, allowing the differentiation process to be more controlled, and the resulting cell population may be more uniform (see, e.g., WO 01/51616; US 2002/0151053 A1).

Notwithstanding the advantages of the direct differentiation method, in certain embodiments, the human pluripotent stem cells may be differentiated into islet-like cells through the formation of aggregates at some point in the differentiation protocol. In certain embodiments, those aggregates are clusters. In certain embodiments, the aggregates are embryoid bodies. In certain embodiments, both embryoid bodies and clusters form during the differentiation (at different stages).

In certain embodiments, the culture medium used during the differentiation steps is serum-free. In various embodiments, the culture medium used during the differentiation steps contains less than 0.25% serum, or less than 0.5% serum, or less than 1.0% serum, or less than 2.0% serum, or less than 5.0% serum, or less than 10% serum.

In certain embodiments, the differentiating cells are cultured on a substrate. Substrates include, but are not limited to collagen, laminin, fibronectin, vitronectin, hyaluronate poly-L-lysine-coated tissue culture plastic, and Matrigel.

Certain solid surfaces may be used in the culturing of cells. Those solid surfaces include, but are not limited to, standard cell culturing plates such as 6-well, 24-well, 96-well, or 144-well plates. Certain solid surfaces also include, but are not limited to, microcarriers and disks. In certain embodiments, the microcarriers are beads. Beads come in various forms, including but not limited to, Cytodex dextran microcarrier beads with positively charged groups, gelatin/collagen-coated beads, and macroporous microcarrier beads with different porosities. Various beads, including Cytodex dextran microcarrier beads, gelatin-coated beads, and macroporous microcarrier beads are commercially available from, e.g., Sigma-Aldrich, St. Louis, Mo. and/or Solohill Engineering Inc., Ann Arbor, Mich. In certain embodiments, the beads are 90-200 µm in size with a total area of 350-500 cm$^2$. In certain embodiments, disks may be used in stirred-tank bioreactors to attach the cells. Disks are commercially available from, e.g., New Brunswick Scientific Co, Inc. (Edison, N.J.). In certain embodiments, the disks are Fibra-cel disks (New Brunswick Scientific Co.), which are polyester/polypropylene disks. A gram of Fibra-cel disks provides a surface area of 1200 cm$^2$.

The solid surface may be made of a variety of substances including, but not limited to, glass or plastic. Plastics include, but are not limited to, polystyrene, polyvinylchloride, polycarobnate, polytetrafluorethylene, melinex, and thermanox. In certain embodiments, the solid surface is three-dimensional in shape. Exemplary three-dimensional solid surfaces are described, e.g., in US 2005/0031598.

In certain embodiments, the cells are in a single-cell suspension. The single-cell suspension may be cultured in various bioreactors including, but not limited to, spinner flasks, shaker flasks, and fermentors. Exemplary fermentors include, but are not limited to, Celligen Plus (New Brunswick Scientific Co, Inc., Edison, N.J.), and the Stirred-Tank Reactor (STR; Applikon Inc., Foster City, Calif.). In certain embodiments, the bioreactors may be continuously perfused with media or may be used in a fed-batch mode. Bioreactors come in various sizes, for example, 2.2 L, 5 L, 7.5 L, 14 L and 20 L.

Enrichment of Islet-Like Cells Differentiated from Human Pluripotent Stem Cells

Figure 4:
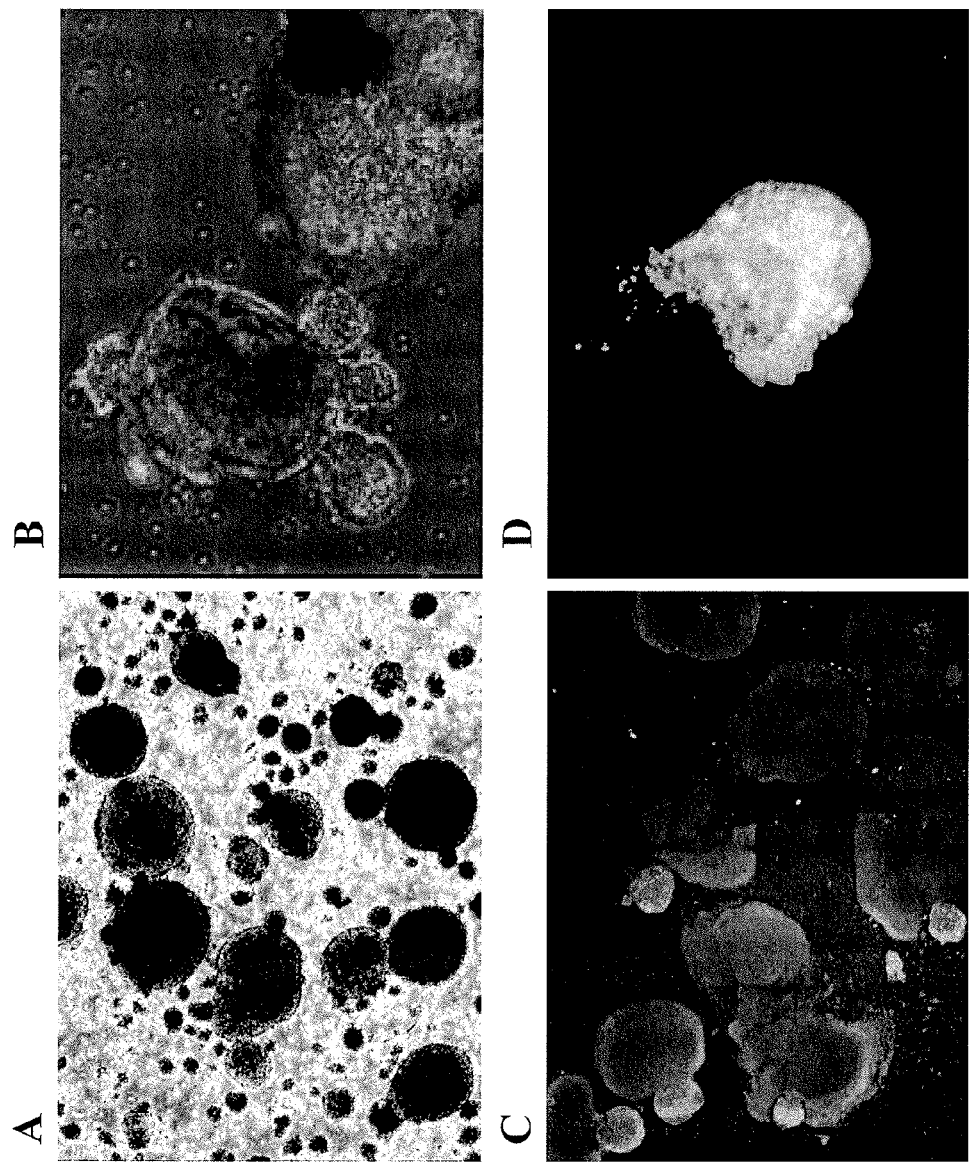
FIG. 4—Clusters and buds from a day 36 cell population from a differentiation of human embryonic stem cells to islet-like cells. (A-B) Phase-contrast micrograph (4× and 10×); (C-D) Human C-peptide staining (4× and 10×). It can be seen that the C-peptide staining occurs primarily in the buds.

This invention provides, inter alia, methods for enriching the proportion of islet-like cells, which include insulin-producing cells and glucagon-producing cells, in a cell population obtained by differentiating human pluripotent stem cells. In certain embodiments of the differentiation, the cells are cultured in a suspension phase, creating cell clusters. Buds form on at least some of those cell clusters, and cells expressing certain pancreatic endocrine markers are present in higher proportions in the buds than in the clusters (see, e.g., FIG. 4). Furthermore, the size of the buds formed on the clusters during the differentiation are smaller than the clusters, providing a means for enriching the cell population by separating the cell clusters and buds into different fractions based, for example, on the relative size differences.

In addition, the inventors hypothesize that there is a density difference between the buds and the clusters, which provides additional means of separating the buds from the clusters. For example, differential centrifugation may be used to separate the buds from the clusters.

An exemplary enrichment method for the islet-like cells is as follows. A differentiation of human embryonic stem cells to islet-like cells forms a cell population comprising clusters, wherein buds have formed on at least some of the clusters. At least some of the buds are dissociated from their clusters by repeated pipetting, and the dissociated buds and clusters are separated by a 70 micron nylon mesh into two fractions—the fraction that passed through the 70 micron nylon mesh and the fraction that is retained by the mesh and which is subsequently washed from the mesh. The fraction that passed through the 70 micron mesh is called the equal to or less than 70 micron fraction. The retained fraction is washed from the filter and passed through a 200 micron mesh, forming two further fractions—the fraction that passes through the 200 micron mesh and the fraction retained by the mesh. The fraction that passes through the 200 micron mesh is called the 70 to 200 micron fraction. The cells retained on the 200 micron mesh are washed off and form the greater than 200 micron fraction.

In certain embodiments, the cell population from the differentiation of human pluripotent stem cells is only passed through a 200 micron mesh, thus forming an equal to or less than 200 micron fraction and greater than 200 micron fraction. In one such experiment, it was found that the equal to or less than 200 micron fraction contains about a 5-fold enrichment in insulin protein content relative to the greater than 200 micron fraction (see Example 4).

In certain embodiments, the cell population is separated into fractions based on size differences using a size separation value of 200 microns. In certain embodiments, the size separation value is 150 microns. In certain embodiments, the size separation value is 70 microns. In certain embodiments, the size separation value is between 20 microns and 500 microns. In certain embodiments, the size separation value is between 100 and 300 microns.

In certain embodiments, the cell population is separated into three fractions. In certain embodiments the cell population is separated into four fractions. In certain embodiments, the cell population is separated into more than four fractions.

In certain embodiments, the cell population is separated into two fractions of which one has a higher proportion of islet-like cells. In certain embodiments, the cell population is separated into three fractions, and two of the fractions, each having a higher proportion of islet-like cells than the third fraction, are combined to form an enriched fraction. In certain embodiments, the cell population is separated into more than three fractions, and two or more of the fractions are then recombined to form an enriched fraction. In certain embodiments, the cell population is separated into more than two fractions, and only one fraction is considered the enriched fraction. In certain embodiments, the enriched fraction or fractions have a smaller particle size than at least one other fraction resulting from the separation step.

In certain embodiments, buds are separated from clusters using a separation value of 20 microns, followed by a fractionation of the greater than 20 micron fraction using a size separation value of 200 microns. In those embodiments, the 20 to 200 micron fraction contains a higher proportion of islet-like cells than the equal to or less than 20 micron fraction and than the greater than 200 micron fraction.

In certain embodiments, buds are separated from clusters using a size separation value of 50 microns, followed by a fractionation of the greater than 50 micron fraction using a size separation value of 200 microns. In those embodiments, the 50 to 200 micron fraction contains a higher proportion of insulin-secreting cells than the equal to or less than 50 micron fraction and than the greater than 200 micron fraction.

In certain embodiments, further enrichment steps are performed on the enriched fraction from the separation step. In certain embodiments, the further enrichment step is a size separation step. In certain embodiments, the further enrichment step involves sorting the cells by use of a marker expressed by the desired cells.

Because the buds physically form on the clusters, it may be necessary to dissociate at least some of the buds from their clusters before the separation step. In certain embodiments, the buds are dissociated from the clusters by mechanical force, such as, but not limited to, repeated pipetting. In certain embodiments, the buds are dissociated from the clusters through use of an enzyme such as, but not limited to, Dispase or trypsin. The timing and amount of any enzyme treatment should be carefully determined to minimize any dissociation of the buds and of the clusters themselves. It is noted that some buds may dissociate from their clusters in the normal course of passaging the cells (see, e.g., FIG. 5), and so dissociation may not be required before the separation step to achieve enrichment.

The invention is not limited to any certain technique for separating the buds from the clusters. For example, various known methods of separating cell populations by size may be used in the practice of the invention.

Many methods are available for separating cells and tissues by size. For example, a mesh, e.g. nylon, may be used. Commercial mesh products include, but are not limited to, Filcon filters (BD Biosciences) and Spectrum Spectra/Mesh Woven Polymer Macrofiltration Squares (Fisher Scientific).

In certain embodiments, the buds may be separated from the clusters based on the relative size differences through use of flow cytometry. For example, one could use the COPAS flow cytometry instrument (Union Biometrica), which can sort objects in sizes from 40 microns to 1500 microns in size (see, e.g., Fernandez et al, Transplantation 80(6):729-37 (2005)).

In certain embodiments, the smaller buds can be selectively separated from the larger clusters through use of manual or robotic picking. For example, one could use the ClonePix automated cell colony picker (Genetix USA, Inc., Boston, Mass.) or the Pick-in Master PM-1s Colony Picker (B-Bridge International, Inc., Sunnyvale, Calif.).

In certain embodiments, the buds may be separated from the clusters based on the hypothesized density differences using techniques such as, but not limited to, differential centrifugation. Differential centrifugation includes, but is not limited to, gradient centrifugation. Gradient centrifugation methods that may be used include, but are not limited to, Ficoll, Percoll, and Biocoll (Biochrom AG, Berlin, Germany). In certain embodiments, an iodixanol density gradient may be used to separate the buds from the clusters (see, e.g., van der Burg et al., The Scientific World Journal 3:1154-9 (2003)). In certain embodiments, differential centrifugation is performed without the use of a gradient. For example, one could determine the centrifugal force at which the clusters would sediment, but at which the buds would remain in suspension. Once the force is determined, the cell population can be centrifuged at that force to sediment the clusters, while leaving the buds in the suspension phase.

In certain embodiments, the buds may be separated from the clusters based on the differential in sensitivity of the buds and clusters to shear forces in the culture medium when those particles are attached to a substrate. Because the clusters are generally larger than the buds, they are less likely to remain attached to the substrate when shear forces are applied, for example, by swirling the container such that the culture fluid moves horizontally relative to the substrate. Careful titration of the shear forces should be done in order to differentially detach the clusters. Thus, one could then remove the culture fluid after application of the appropriate shear forces. Then, a more vigorous washing of the substrate could be done to obtain a fraction enriched in the buds (and therefore the islet-like cells).

Islet-Like Cells Having Certain Genetic Alterations

Islet-like cells containing one or more genetic alterations can be made by genetic engineering of the cells either before or after differentiation (see, e.g., U.S. 2002/0168766 A1). For example, cells can be modified in such a way as to increase their replication potential by genetically altering the cells to express telomerase reverse transcriptase. Particularly suitable is the catalytic component of human telomerase (hTERT), provided in International Patent Application WO 98/14592. Transfection and expression of telomerase in human cells is described in Bodnar et al., Science 279:349, 1998 and Jiang et al., Nat. Genet. 21:111, 1999. Genetically altered cells can be assessed for hTERT expression by RT-PCR, telomerase activity (TRAP assay), immunocytochemical staining for hTERT, or replicative capacity, according to standard methods.

Other methods of immortalizing cells are also contemplated, such as transforming the cells with DNA encoding myc, the SV40 large T antigen, or MOT-2 (U.S. Pat. No. 5,869,243, International Patent Applications WO 97/32972 and WO 01/23555). Such modifications can be made, e.g., before or after the cells progress to restricted developmental lineage cells or terminally differentiated cells (see, e.g., U.S. Publication No. 2003/0022367 A1).

In certain embodiments, islet-like cells can be genetically altered in order to enhance their ability to be involved in tissue regeneration and/or to deliver a therapeutic gene to a site of administration. As a nonlimiting example, a vector may be designed to express the desired gene by linking its coding sequence to a promoter that is either pan-specific or specifically active in the differentiated cell type. In certain embodiments, expression of particular genes at the site of islet-like cell administration may facilitate adoption of the functional β-islet cell phenotype, enhance the beneficial effect of the administered cell, and/or increase proliferation and/or activity of host cells neighboring the treatment site.

If desired, the cells of this invention can be prepared or further treated to remove undifferentiated cells in vitro, or to safeguard against revertants in vivo. One way of depleting undifferentiated stem cells from the population is to transfect the population with a vector in which an effector gene under control of a promoter that causes preferential expression in undifferentiated cells—such as the TERT promoter or the OCT-4 promoter. The effector gene may be a reporter to guide cell sorting, such as green fluorescent protein. The effector may be directly lytic to the cell, encoding, for example, a toxin, or a mediator of apoptosis, such as caspase (Shinoura et al., Cancer Gene Ther. 7:739, 2000). The effector gene may have the effect of rendering the cell susceptible to toxic effects of an external agent, such as an antibody or a prodrug. Exemplary is a herpes simplex thymidine kinase (tk) gene, which causes cells in which it is expressed to be susceptible to ganciclovir. Alternatively, the effector can cause cell surface expression of a foreign determinant that makes any cells that revert to an undifferentiated phenotype susceptible to naturally occurring antibody in vivo.

Uses of Islet-Like Cells

Animal Model Experiments

Of considerable interest for the purposes of islet cells for clinical application is the ability of cell populations to reconstitute the islet system of a host animal. Reconstitution can be tested using several well-established animal models.

The non-obese diabetic (NOD) mouse carries a genetic defect that results in insulitis showing at several weeks of age (Yoshida et al., Rev. Immunogenet. 2:140, 2000). 60-90% of the females develop overt diabetes by 20-30 weeks. The immune-related pathology appears to be similar to that in human Type I diabetes. Other models of Type I diabetes are mice with transgene and knockout mutations (Wong et al., Immunol. Rev. 169:93, 1999). A rat model for spontaneous Type I diabetes was recently reported by Lenzen et al. (Diabetologia 44:1189, 2001). Hyperglycemia can also be induced in mice (>500 mg glucose/dL) by way of a single intraperitoneal injection of streptozotocin (Soria et al., Diabetes 49:157, 2000), or by sequential low doses of streptozotocin (Ito et al., Environ. Toxicol. Pharmacol. 9:71, 2001). To test the efficacy of implanted islet cells, the mice are monitored for return of glucose to normal levels (<200 mg/dL).

Larger animals provide a good model for following the sequelae of chronic hyperglycemia. Dogs can be rendered insulin-dependent by removing the pancreas (J. Endocrinol. 158:49, 2001), or by feeding galactose (Kador et al., Arch. Opthalmol. 113:352, 1995). There is also an inherited model for Type I diabetes in keeshond dogs (Am. J. Pathol. 105:194, 1981).

By way of illustration, a pilot study can be conducted using hPS derived islet cells in the following animals: a) non-diabetic nude (T-cell deficient) mice; b) nude mice rendered diabetic by streptozotocin treatment; and c) nude mice in the process of regenerating islets following partial pancreatectomy. The number of cells transplanted is equivalent to ~1000-2000 normal human islets, implanted under the kidney capsule, in the liver, or in the pancreas. For non-diabetic mice, the endpoints of can be assessment of graft survival (histological examination) and determination of insulin production by biochemical analysis, RIA, ELISA, and immunohistochemistry. Streptozotocin treated and partially pancreatectomized animals can also be evaluated for survival, metabolic control (blood glucose) and weight gain.

Use of Islet Cells in Research and Clinical Therapy

This invention provides a method to produce large numbers of islet precursor cells, and mature islet cells. These cell populations can be used for a variety of important research, development, and commercial purposes.

The cells of this invention can be used to prepare a cDNA library relatively uncontaminated with cDNA preferentially expressed in cells from other lineages. The differentiated cells of this invention can also be used to prepare monoclonal or polyclonal antibodies that are specific for markers of islet precursors and their derivatives, according to standard methods.

Of particular interest are use of the compositions of this invention for drug development and clinical therapy.

Drug Screening

Islet cells of this invention can be used to screen for factors (such as solvents, small molecule drugs, peptides, polynucleotides) or environmental conditions (such as culture conditions or manipulation) that affect the characteristics of islet precursor cells and their various progeny.

A prime example is the use of islet cell clusters or homogeneous beta cell preparations for the effect of small molecule drugs that have the potential to up- or down-regulate insulin synthesis or secretion. The cells are combined with the test compound, and then monitored for change in expression or secretion rate, for example by RT-PCR or immunoassay of the culture medium.

Other screening methods of this invention relate to the testing of pharmaceutical compounds for a potential effect on islet cell growth, development, or toxicity. This type of screening is appropriate not only when the compound is designed to have a pharmacological effect on islet cells, but also to test for islet-related side-effects of compounds designed for a primary pharmacological effect elsewhere.

In a third example, hPS cells (undifferentiated or differentiated) are used to screen factors that promote maturation into islet cells, or promote proliferation and maintenance of islet cells in long-term culture. For example, candidate differentiation factors or maturation factors are tested by adding them to cells in different wells, and then determining any phenotypic change that results, according to desirable criteria for further culture and use of the cells. This can lead to improved derivation and culture methods for not only hPS derived islets, but also for islet cells and their progenitors isolated from pancreas.

The reader is referred generally to the standard textbook, *In vitro Methods in Pharmaceutical Research*, Academic Press, 1997, and U.S. Pat. No. 5,030,015. Assessment of the activity of candidate pharmaceutical compounds generally involves combining the differentiated cells of this invention with the candidate compound, either alone or in combination with other drugs. The investigator determines any change in the morphology, marker phenotype, or functional activity of the cells that is attributable to the compound (compared with untreated cells or cells treated with an inert compound), and then correlates the effect of the compound with the observed change.

Cytotoxicity can be determined in the first instance by the effect on cell viability, survival, morphology, and the expression of certain markers and receptors. Effects of a drug on chromosomal DNA can be determined by measuring DNA synthesis or repair. [$^3$H]-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (pp 375-410 in "In vitro Methods in Pharmaceutical Research," Academic Press, 1997) for further elaboration.

Reconstitution of Islet Function

This invention also provides for the use of islet precursor cells or their derivatives to restore islet function in a patient in need of such therapy. Any condition relating to inadequate production of a pancreatic endocrine (insulin, glucagon, or somatostatin), or the inability to properly regulate secretion may be considered for treatment with cells prepared according to this invention, as appropriate. Of especial interest is the treatment of Type I (insulin-dependent) diabetes mellitus.

Patients are chosen for treatment based on confirmed long-term dependence on administration of exogenous insulin, and acceptable risk profile. The patient receives approximately 10,000 islet equivalents per kg body weight. To overcome an allotype mismatch, the patient is started before surgery with anti-rejection drugs such as FK506 and rapamycin (orally) and daclizumab (intravenously). The islet cells are infused through a catheter in the portal vein. The patient is then subjected to abdominal ultrasound and blood tests to determine liver function. Daily insulin requirement is tracked, and the patient is given a second transplant if required. Follow-up monitoring includes frequent blood tests for drug levels, immune function, general health status, and whether the patient remains insulin independent.

General approaches to the management of the diabetic patient are provided in standard textbooks, such as the *Textbook of Internal Medicine*, 3$^{rd}$ Edition, by W. N. Kelley, Ed., Lippincott-Raven, 1997; and in specialized references such as *Diabetes Mellitus: A Fundamental and Clinical Text*, 2nd Edition, by D. Leroith, Ed., Lippincott Williams & Wilkins, 2000; *Diabetes (Atlas of Clinical Endocrinology Vol. 2)*, by C. R. Kahn et al., Eds., Blackwell Science, 1999; and *Medical Management of Type 1 Diabetes*, 3$^{rd}$ Edition, McGraw Hill, 1998. Use of islet cells for the treatment of Type I diabetes is discussed at length in *Cellular Inter-Relationships in the Pancreas: Implications for Islet Transplantation*, by L. Rosenberg et al., Chapman & Hall, 1999; and *Fetal Islet Transplantation*, by C. M. Peterson et al., Eds., Kluwer, 1995.

For purposes of commercial distribution, islet cells of this invention are typically supplied in the form of a pharmaceutical composition, comprising an isotonic excipient prepared under sufficiently sterile conditions for human administration. This invention also includes sets of cells that exist at any time during their manufacture, distribution, or use. The cell sets comprise any combination of two or more cell populations described in this disclosure, exemplified but not limited to a type of differentiated hPS-derived cell (islet cells, their precursors, subtypes, and so on), in combination with undifferentiated hPS cells or other differentiated cell types, sometimes sharing the same genome. Each cell type in the set may be packaged together, or in separate containers in the same facility, or at different locations, under control of the same entity or different entities sharing a business relationship.

For general principles in medicinal formulation of cell compositions, the reader is referred to *Cell Therapy: Stem Cell Transplantation, Gene Therapy, and Cellular Immunotherapy*, by G. Morstyn & W. Sheridan, Eds., Cambridge University Press, 1996. The composition is optionally packaged in a suitable container with written instructions for a desired purpose, such as the treatment of diabetes.

Devices

The cells of this invention can also be used as the functional component in a mechanical device designed to produce one or more of the endocrine polypeptides of pancreatic islet cells.

In its simplest form, the device contains the hPS derived islet cells behind a semipermeable membrane that prevents passage of the cell population, retaining them in the device, but permits passage of insulin, glucagon, or somatostatin secreted by the cell population. This includes islet cells that are microencapsulated, typically in the form of cell clusters to permit the cell interaction that inhibits dedifferentiation. For example, U.S. Pat. No. 4,391,909 describe islet cells encapsulated in a spheroid semipermeable membrane made up of polysaccharide polymers >3,000 mol. wt. that are cross-linked so that it is permeable to proteins the size of insulin, but impermeable to molecules over 100,000 mol. wt. U.S. Pat. No. 6,023,009 describes islet cells encapsulated in a semipermeable membrane made of agarose and agaropectin. Microcapsules of this nature are adapted for administration into the body cavity of a diabetic patient, and are thought to have certain advantages in reducing histocompatibility problems or susceptibility to bacteria.

More elaborate devices are also contemplated, either for implantation into diabetic patients, or for extracorporeal therapy. U.S. Pat. No. 4,378,016 describes an artificial endocrine gland containing an extracorporeal segment, a subcutaneous segment, and a replaceable envelope containing the hormone-producing cells. U.S. Pat. No. 5,674,289 describes a bioartificial pancreas having an islet chamber, separated by a semipermeable membrane to one or more vascularizing chambers open to surrounding tissue. Useful devices typically have a chamber adapted to contain the islet cells, and a chamber separated from the islet cells by a semipermeable membrane which collects the secreted proteins from the islet cells, and which may also permit signaling back to the islet cells, for example, of the circulating glucose level.

All publications and patents mentioned in this application are herein incorporated by reference for any purpose.

EXAMPLES

Example 1

Differentiation of Human Embryonic Stem Cells into Islet-Like Cells

H1 human embryonic stem (hES) cells were passaged and cultured in T225 flasks that had been coated with growth factor-reduced Matrigel (BD Biosciences Cat #356231) as described in Xu, C. et al., Nat. Biotechnol. 19(10):971 (2001), for seven days in MEF CM+bFGF ("Culture Medium A"). 75 ml of Culture Medium A was added to each flask.

On day one of the protocol, the medium of the hES cell culture was changed to 75 ml per flask of RPMI 1640/B27 supplemented with 1 mM sodium butyrate and 52 ng/ml Activin A ("Culture Medium B"). On day two, the medium was changed to 75 ml per flask of RPMI 1640/B27 supplemented with 0.5 mM sodium butyrate and 52 ng/ml Activin A ("Culture Medium C"). On days three through seven, the cells were refed every 1-2 days with Culture Medium C at 75 ml per flask.

transcribed into cDNA with Random Hexamers and Superscript II (Invitrogen). Each PCR reaction contains Universal Taqman PCR mix, 300 nM probe and 200 nM of each forward and reverse primers, and an added 1× cyclophillin endogenous control (Applied Biosystems Inc.). The primers and probes used are listed in Table 1 (SEQ ID NOS:1-12). Quantitative real-time PCR was performed on the ABI PRISM 7900HT Sequence Detection System (Applied Biosystems) using software SDS 2.1. The cycling conditions are 40 cycles of: 2 minutes at 50° C., 10 minutes at 95° C., 15 seconds at 95° C. and 1 minute at 60° C.

TABLE 1

Primer and Probe Sequences

| Gene | Forward primer (5' to 3') | Reverse primer (5' to 3') | Taqman probe (5'-FAM to 3'-Tam) | Reference sequence |
| --- | --- | --- | --- | --- |
| Pdx1 | CCTTTCCCATGGATGAAGTC (SEQ ID NO: 1) | CGTCCGCTTGTTCTCCTC (SEQ ID NO: 5) | AAGCTCACGCGTGGAAAGGCC (SEQ ID NO: 9) | NM_000209 |
| Ngn3 | TCTCTATTCTTTTGCGCCGG (SEQ ID NO: 2) | CTTGGACAGTGGGCGCAC (SEQ ID NO: 6) | AGAAAGGATGACGCCTCAACCCTCG (SEQ ID NO: 10) | NM_020999 |
| Insulin | GGGAGGCAGAGGACCTG (SEQ ID NO: 3) | CCACAATGCCACGCTTCT (SEQ ID NO: 7) | AGGTGGGGCAGGTGGAGCTG (SEQ ID NO: 11) | NM_000207 |
| Glucagon | GCTGCCAAGGAATTCATTGC (SEQ ID NO: 4) | CTTCAACAATGGCGACCTCTTC (SEQ ID NO: 8) | TGAAAGGCCGAGGAAGGCGAGATT (SEQ ID NO: 12) | NM_002054 |
| Gene | Sources | | Reference sequence | |
| Nkx6.1 | Applied Biosystems Cat# Hs00232355-m1 | | NM_006168.1 | |
| Glut-2 | Applied Biosystems Cat# Hs00165775-m1 SLC2A2 | | NM_000340.1 | |

On day 8, the cells were treated with 15 ml/T225 flask of 200 U/ml collagenase IV for 5 minutes at 37° C. Then, 20 ml of RPMI 1640/B27 supplemented with 2 ng/ml FGF-2, 20 ng/ml EGF, and 100 ng/ml Noggin ("Culture Medium D") was added to each flask. The cells were scraped with a pipette and then pipetted gently off the flask and transferred to a 50-ml tube. Each flask was then washed with an additional 16 ml of Culture Medium D, and the resulting wash was added to the 50-ml tube. The resulting cell clumps were triturated by pipetting up and down 4-8 times to break the clumps into smaller pieces. The suspension was then transferred into ultra-low attachment 6-well plates at 2 ml per well. 2 additional ml of Culture Medium D was added to each well. The plate was incubated overnight at 37° C.

Between days 9 and 21, the cells were cultured in suspension in Culture Medium D with refeedings every 2-3 days. On day 22, the medium was replaced with Culture Medium D without the FGF-2 ("Culture Medium E"). The cells were then cultured in suspension for 7 days with refeedings every 2-3 days.

On day 29, the medium was changed to RPMI 1640 supplemented with 0.5% BSA, 10 mM nicotinamide (Sigma), and 50 ng/ml IGF-II ("Culture Medium F") at 4 ml per well. The cells were cultured in this medium in suspension for 5 days with refeedings every 2-3 days. On day 34, the medium was changed to RPMI 1640 supplemented with 0.5% BSA and 10 mM Nicotinamide ("Culture Medium G") at 4 ml per well. The cells were cultured in this medium until day 36.

Figure 2:
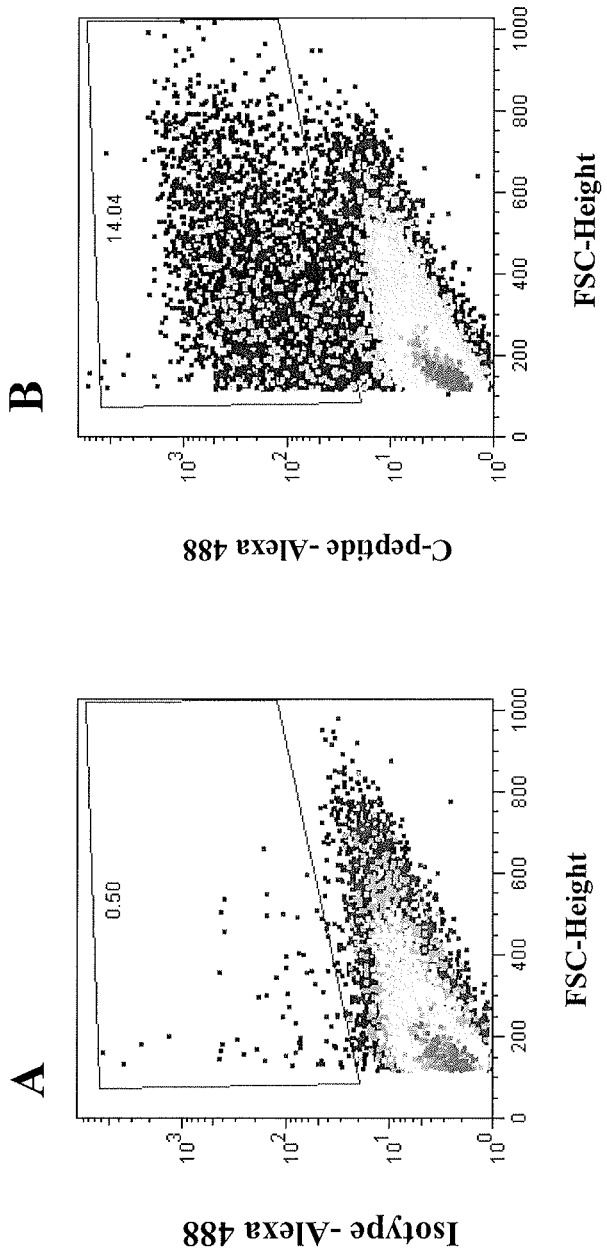
FIG. 2—C-peptide expression of one differentiation of human embryonic stem cells to islet-like cells using flow cytometry. The cell population at day 36 was treated with trypsin-EDTA and stained as in FIG. 1, except that 0.1 ug/0.5 million cells of the anti-C-peptide and anti-glucagon antibodies were used. The stained cells were then analyzed by FACScaliber with CellQuest software.
Figure 3:
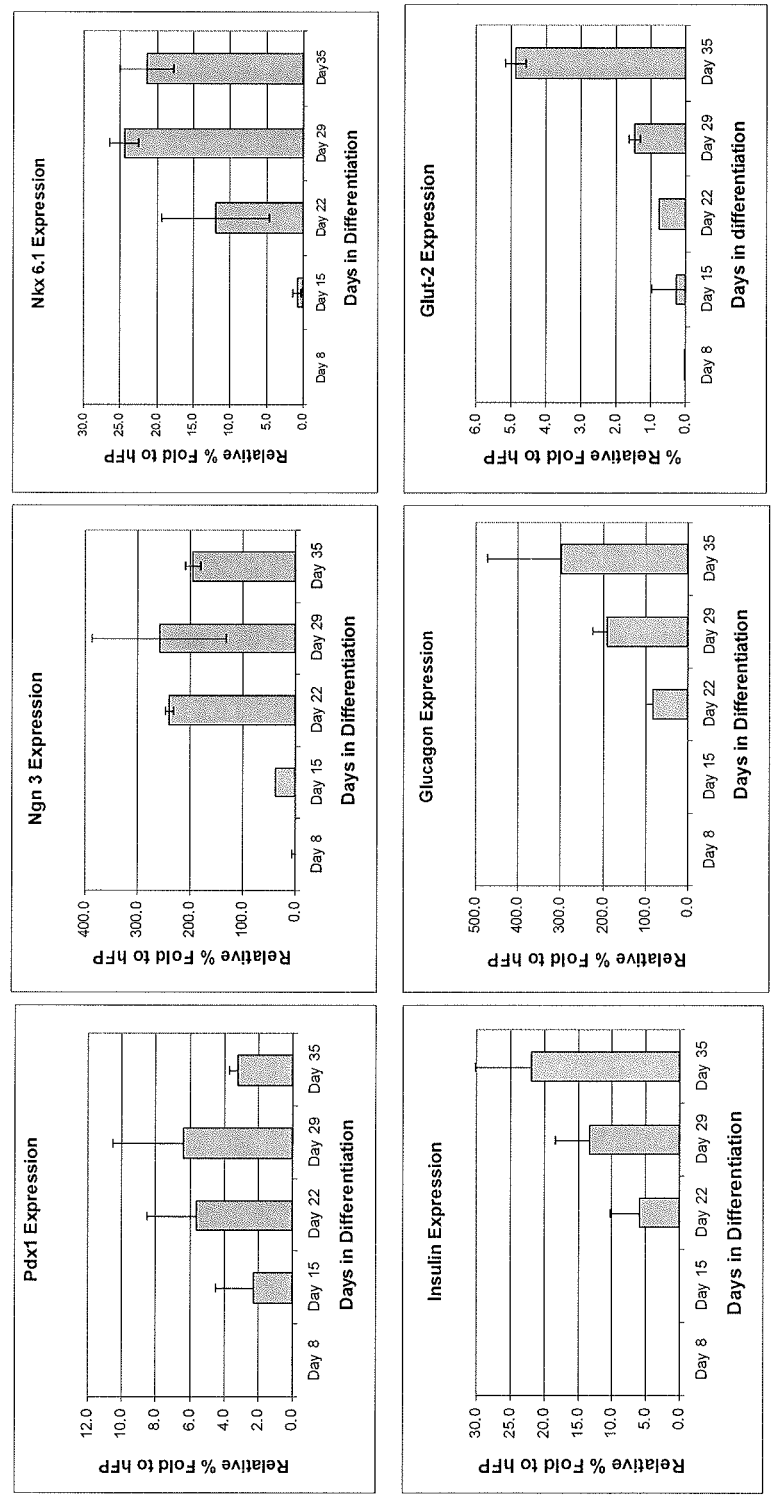
FIG. 3—Kinetic gene expression of pancreatic lineage genes during one differentiation of human embryonic stem cells to islet-like cells. Total mRNA samples were collected at day 8, 15, 22, 29 and 35 differentiation, and real-time PCR analysis was performed to quantify the expression levels of PDX1, ngn3, Nkx 6.1, insulin, glucagon and glut-2. For each gene, the level of expression is normalized to cyclophilin and was compared to an 18-20 week human fetal pancreas control as relative percentage fold.

Total RNA was isolated from the day 36 cell population using an RNeasy mini kit (Qiagen), and any contaminating genomic DNA was removed by digestion with deoxyribonuclease I (Invitrogen). Two microgram of RNA was reverse- The results of one differentiation are shown in FIGS. 1-3. FIG. 1 shows immunofluorescent C-peptide and glucagon staining of islet-like clusters that resulted from the differentiation. C-peptide is a by-product peptide of the cleavage of the precursor form of insulin (pro-insulin) to the active insulin form, and thus its presence evidences insulin-production. This data indicates that the differentiation results in insulin-producing cells and glucagon-producing cells. FIG. 2 shows the FACS analysis of the resulting day 36 cell population from the differentiation. That analysis demonstrates that 13.5% of the cells expressed C-peptide. FIG. 3 shows the expression of certain genes at various stages of the differentiation as determined by RT-PCR performed as described above. It can be seen that the levels of insulin and glucagon RNA increase as the differentiation progresses. In addition, the expression of the glucose transporter (Glut-2) RNA, which is a necessary component of glucose responsiveness, also increases as the differentiation progresses.

Example 2

Size Separation Enrichment of Islet-Like Cells

Day 36 cells from a different differentiation of hES cells, performed according to the protocol in Example 1, were collected into an empty 50-ml tube. That cell population contained clusters that had buds formed on their surfaces (see FIGS. 4a and 4b). Immunofluorescent staining of the cluster/bud structures demonstrated that C-peptide expression segregated into the buds (see FIGS. 4c and 4d).

Figure 5:
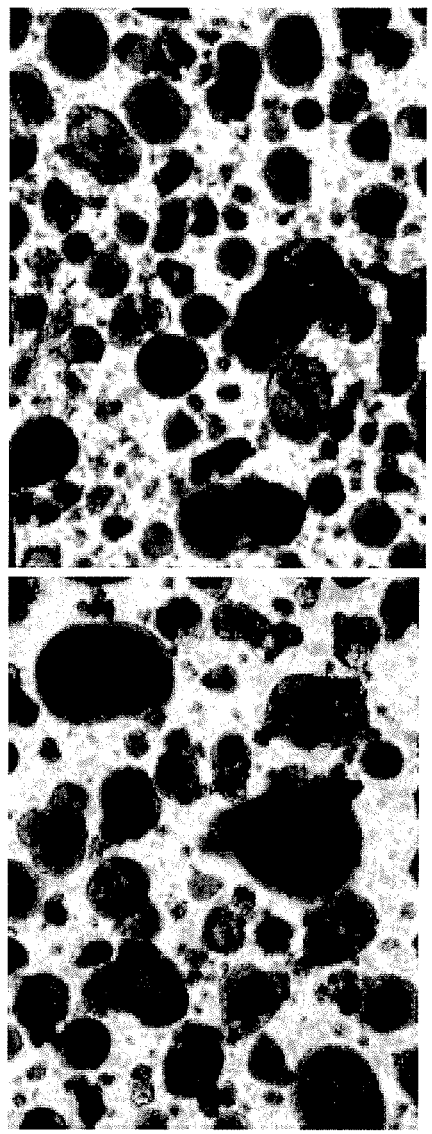
FIG. 5—A phase-contrast micrograph (4×) of the day 36 cell population from a differentiation of human embryonic stem cells to islet-like cells showing clusters with buds formed on the surface of certain of the clusters. Deliberate dissociation of buds and clusters had not been performed on this population.

The day 36 cell population was pipetted 15-20 times with a 25-ml pipette to break apart the cell clusters and buds. FIG. 5 shows micrographs of the cell population before the pipetting step. It can be seen that some of the buds are dissociated from their clusters prior to the pipetting step.

The resulting cell population was then slowly loaded onto a 70 micron mesh (VWR (BD Biosciences) Catalog #21008-952), placed on top of a 50-ml centrifuge tube, and the medium was allowed to pass through the mesh. The mesh was washed by passing 20 ml of the Culture Medium G through the mesh. The mesh was removed, and the cells in the pass-through fraction were spun down and resuspended in the Culture Medium G. These cells were called the "equal to or less than 70 micron fraction."

The 70 micron mesh used in the 70 micron separation was then placed on top of another 50-ml centrifuge tube in an upside down orientation relative to its orientation in the 70 micron separation step. 15 ml of Culture Medium G was passed through to wash the excluded cells into the 50-ml centrifuge tube. The mesh was further washed with Culture Medium G until no visible cell clusters remained on the mesh. The resulting cell suspension was then slowly loaded onto an autoclaved 200 micron mesh (BioDesign, Inc. of New York, Catalog #N200C) placed on top of a 50-ml centrifuge tube. The medium was allowed to pass through the mesh. The mesh was rinsed by passing through an additional 15 to 20 ml of the Culture Medium G. The mesh was removed, and the cells in the 50-ml tube were spun down and resuspended in the Culture Medium G. These cells were termed the "70 to 200 micron fraction."

Figure 6:
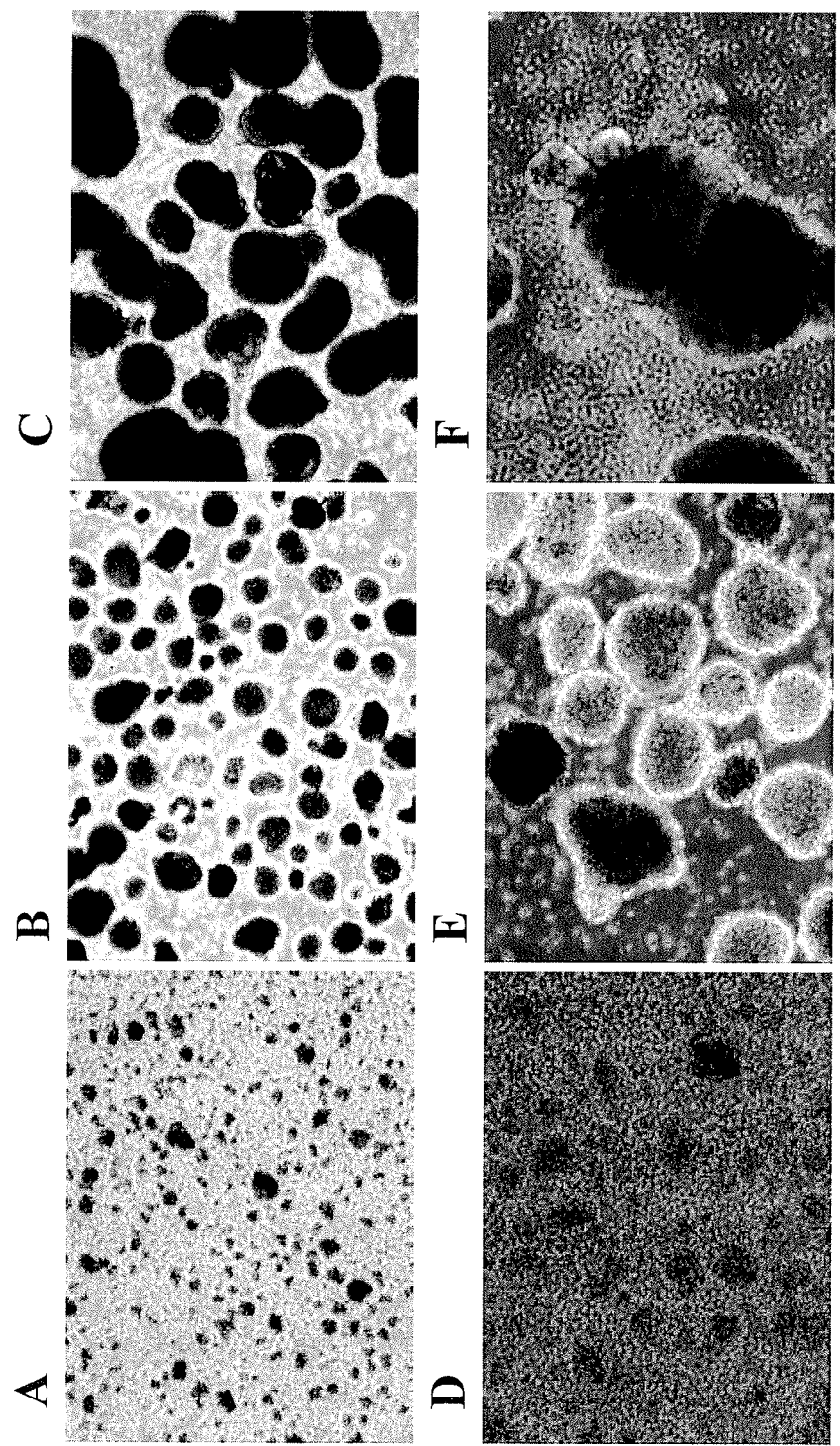
FIG. 6—Phase-contrast micrographs of the three fractions from a two-step size separation of a day 36 cell population from a differentiation of human embryonic stem cells to islet-like cells. Equal to or less than 70 micron fraction (A (4×) and D (10×)); 70 to 200 micron fraction (B (4×) and E (10×)); greater than 200 micron fraction (C (4×) and F (10×)).

The 200 micron mesh used to size select the 70 to 200 micron fraction was then placed on another 50-ml centrifuge tube in an upside down orientation relative to its orientation in the 70 to 200 micron size separation step (i.e., with the cell containing side faced downward). 20 ml of the Culture Medium G was passed through the mesh to wash the cells off the mesh and into the tube. Further Culture Medium G was used to wash the mesh until no cell clumps were visible on the mesh. The resulting cell suspension in the centrifuge tube was then spun down and resuspended in Culture Medium G. Those cells were termed the "greater than 200 micron fraction." FIG. 6 shows micrographs of the three fractions at 4× and at 10× magnifications.

Example 3

Analysis of Size Selected Fractions

RNA was isolated and analyzed using real-time PCR as in Example 1. For the insulin RNA: the day 36 population had an average $C_t$ value of 36.7; the equal to or less than 70 micron fraction had an average $C_t$ value of 32.1; the 70 to 200 micron fraction had an average $C_t$ value of 29.1; and the greater than 200 micron fraction had an average $C_t$ value of 34.6. For the glucagon RNA: the day 36 population had an average $C_t$ value of 29.7; the equal to or less than 70 micron fraction had an average $C_t$ value of 28.5; the 70 to 200 micron fraction had an average $C_t$ value of 24.3; and the greater than 200 micron fraction had an average $C_t$ value of 27.5. The relative quantitation was normalized with Cyclophillin (Applied Biosystems Inc.), and expressed as a relative percentage fold to human fetal pancreas (Stratagene).

Figure 7:
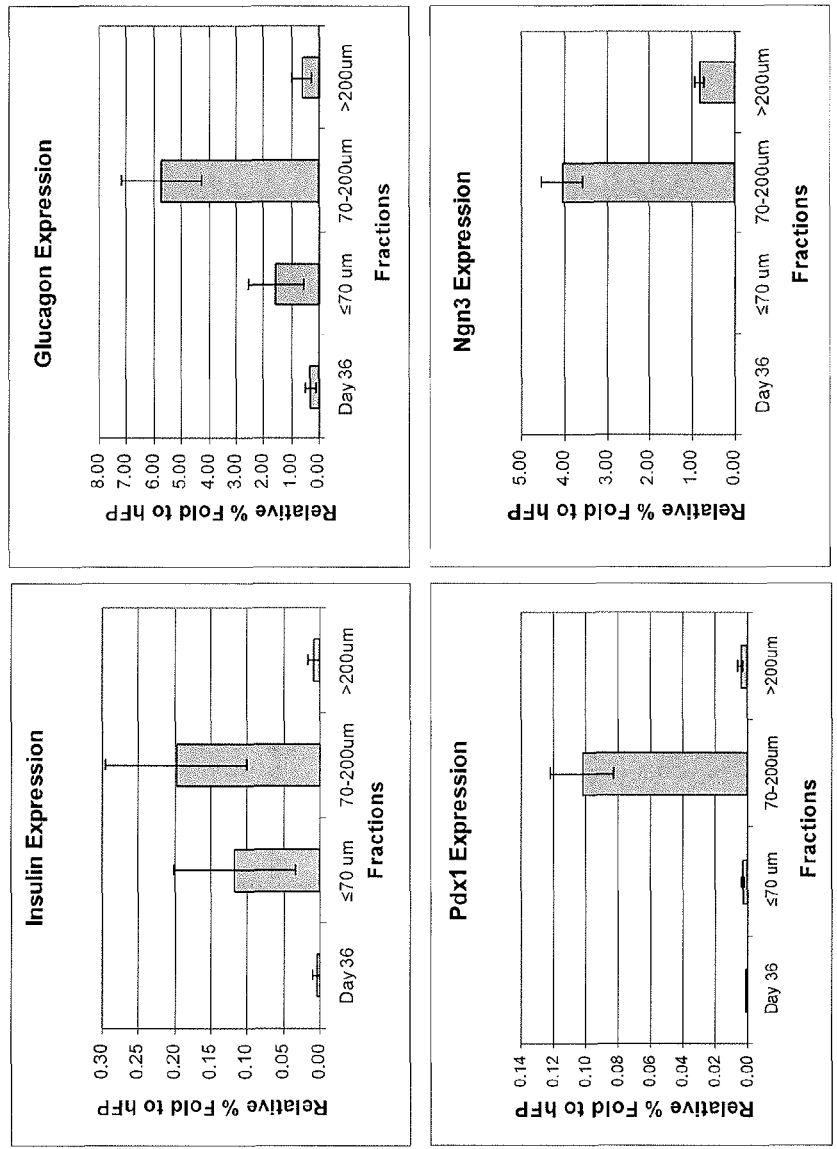
FIG. 7—Gene expression in the day 36 cell population (d36) and the three fractions from a size separation of the day 36 cell population. Gene expression was determined by real-time PCR analysis as described in Example 1: (A) Insulin; (B) Glucagon; (C) Pdx1; (D) Ngn3.

FIG. 7 shows the expression of insulin, glucagon, PDX-1, and Ngn-3 RNAs in the 70 to 200 micron fraction, which demonstrates the segregation, and thus enrichment, of cells expressing those markers into that fraction. The enrichment of the cells in the 70 to 200 micron fraction relative to the day 36 cell population is as follows: insulin-producing cells—about 43-fold higher; and glucagon-producing cells—about 18-fold higher. In addition, it can be seen that cells expressing insulin and glucagon RNAs were also enriched in proportion in the equal to or less than 70 micron fraction with respect to the day 36 cell population as follows: insulin-producing cells—about 25-fold higher; and glucagon-producing cells—about 5-fold higher.

Example 4

Enrichment of Insulin-Production by Size Sorting

H1 human embryonic stem cells were differentiated according to the protocol in Example 1. Day 36 cells were then size sorted as follows.

200 micron mesh was used to fractionate the day 36 cell population. The 200 micron mesh was placed on a 50-ml centrifuge tube, and the day 36 cell population suspension was filtered through the mesh. The resulting cell suspension in the centrifuge tube was then spun down and resuspended in Culture Medium G. Those cells were termed the "equal to or less than 200 micron fraction." This equal to or less than 200 micron fraction was split approximately equally into two 50-ml centrifuge tubes.

The 200 micron mesh was then placed in an upside down orientation in a second 50 ml tube, and 20 ml of Culture Medium G was then passed through the mesh to wash any remaining cells off the mesh and into the tube. Further Culture Medium G was used to wash the mesh until no cell clumps were visible on the mesh. The resulting cell suspension in the centrifuge tube was then spun down and resuspended in Culture Medium G. Those cells were termed the "greater than 200 micron fraction." The greater than 200 micron fraction was split approximately equally into two 50-ml centrifuge tubes.

One tube from each fraction was used for the measurement of insulin protein content by ELISA (Mercodia Ultrasensitive Insulin ELISA). The ELISA assay was performed as instructed in the Mercodia kit.

The other tube from each fraction was used for protein quantification (Pierce MicroBCA Assay). The protein quantification assay was performed as instructed in the Pierce kit. Insulin protein content was calculated based on picogram of insulin per microgram of total protein.

Figure 8:
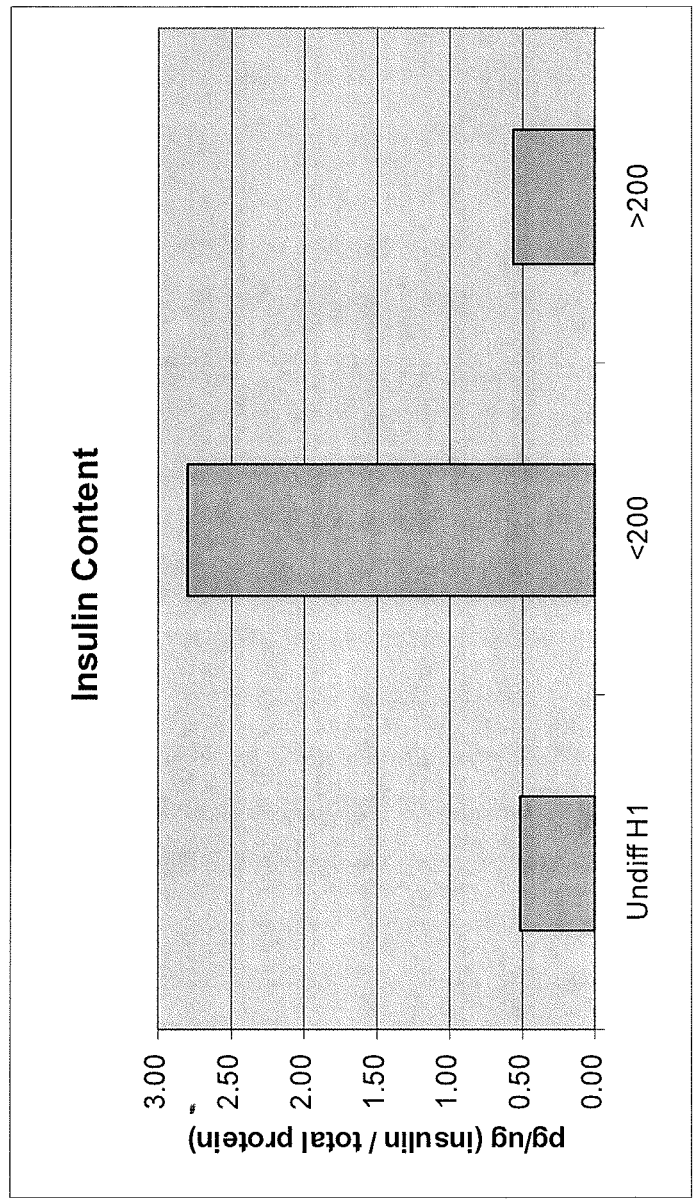
FIG. 8—Insulin content in a population of undifferentiated hES cells and two fractions from a size separation of islet-like cells differentiated from hES cells.

FIG. 8 shows the insulin content of the equal to or less than 200 micron and the greater than 200 micron fractions, as well as from a population of undifferentiated H1 hES cells. The equal to or less than 200 micron contains about 5-fold the level of insulin content per total protein as does the greater than 200 micron fraction.

We claim:

1. A method of enriching the proportion of islet-like cells from a cell population generated by the differentiation of human pluripotent stem cells to islet-like cells, comprising:
   a) differentiating human pluripotent stem cells into a cell population comprising islet-like cells by a method comprising,
      i. contacting human pluripotent stem cells with a first medium comprising Activin A; and
      ii. contacting the cells from step i) with a second medium comprising FGF-2 but lacking Activin A,
      thereby generating a cell population comprising islet-like cells, wherein the cell population comprises cell clusters that have formed buds; and
   b) separating at least some of the buds from at least some of the clusters in the cell population of step (a) into at least two fractions, wherein the fraction containing separated buds contains a higher proportion of insulin or glucagon-producing islet-like cells than the cell population of step (a) and wherein the buds are separated from the clusters based on the size difference between the buds and the clusters.

2. The method of claim 1, wherein the human pluripotent stem cells are human embryonic stem cells.

3. The method of claim 1, wherein the buds are separated from the clusters by use of nylon mesh.

4. The method of claim 3, wherein the nylon mesh is a 200 micron mesh.

5. The method of claim 3, wherein the nylon mesh is a 70 micron mesh.

6. The method of claim 3, wherein the nylon mesh is between 50 and 250 microns.

7. The method of claim 1, wherein at least one of the fractions with a higher proportion of islet-like cells than the cell population of step (a) is a fraction with a smaller particle size than at least one of the other fractions that result from the size separation.

8. The method of claim 7, wherein the at least one fraction with a higher proportion of islet-like cells than the cell population of step (a) has a particle size equal to or less than 200 microns.

9. The method of claim 7 wherein the at least one fraction with a higher proportion of islet-like cells than the cell population of step (a) has a particle size equal to or less than 150 microns.

10. The method of claim 7, wherein the at least one fraction with a higher proportion of islet-like cells than the cell population of step (a) has a particle size equal to or less than 100 microns.

11. The method of claim 1, wherein the cell population of step (a) is fractionated into three fractions by performing two size separation steps, wherein the second separation step is performed on a fraction that results from the first separation step.

12. The method of claim 11, wherein the first separation step is performed using a size separation value equal to or less than 50 microns and the second separation step is performed using a size separation value between 100 microns and 300 microns on the retained fraction from the first separation step; and wherein the pass-through fraction from the second separation step contains a higher proportion of islet-like cells than the cell population of step (a).

13. The method of claim 12, wherein the first separation step is performed using a size separation value of 50 microns and the second separation step is performed using a size separation value of 150 microns, and wherein the 50 to 150 micron fraction contains higher proportion of islet-like cells than the cell population of step (a).

14. The method of claim 11, wherein the first separation step is performed using a size separation value equal to or less than 50 microns and the second separation step is performed using a size separation value between 150 microns and 250 microns on the retained fraction from the first separation step; and wherein the pass-through fraction from the second separation step contains a higher proportion of islet-like cells than the cell population of step (a).

15. The method of claim 14, wherein the first separation step is performed using a size separation value of 50 microns and the second separation step is performed using a size separation value of 200 microns, and wherein the 50 to 200 micron fraction contains higher proportion of islet-like cells than the cell population of step (a).

16. The method of claim 11, wherein the first separation step is performed using a size separation value equal to or less than 20 microns and the second separation step is performed using a size separation value of 100 microns or greater on the retained fraction from the first separation step; and wherein the pass-through fraction from the second separation step contains a higher proportion of islet-like cells than the cell population of step (a).

17. The method of claim 16, wherein the first separation step is performed using a size separation value of 20 microns and the second separation step is performed using a size separation value of 200 microns, and wherein the 20 to 200 micron fraction contains higher proportion of islet-like cells than the cell population of step (a).

18. The method of claim 1, wherein the buds are dissociated from the clusters before the separation step b).

19. The method of claim 18, wherein the buds are dissociated from the clusters by repeated pipetting.

20. The method of claim 18, wherein the buds are dissociated from the clusters by enzyme treatment.

21. The method of claim 20, wherein the enzyme is Dispase.

22. The method of claim 20, wherein the enzyme is trypsin.

23. The method of claim 1, wherein the buds are separated from the clusters by manually or robotically picking the buds.

24. The method of claim 1, wherein the buds are separated from at least some of the clusters using flow cytometry.

* * * * *